(12) United States Patent
Ross

(10) Patent No.: US 12,064,582 B2
(45) Date of Patent: *Aug. 20, 2024

(54) COMPOSITE MICRONEEDLE ARRAY INCLUDING NANOSTRUCTURES THEREON

(71) Applicant: VIVASOR, INC., San Diego, CA (US)

(72) Inventor: Russell Frederick Ross, Jacksonville Beach, FL (US)

(73) Assignee: VIVASOR, INC., San Diego, CA (US)

(*) Notice: Subject to any disclaimer, the term of this patent is extended or adjusted under 35 U.S.C. 154(b) by 583 days.

This patent is subject to a terminal disclaimer.

(21) Appl. No.: 17/029,229

(22) Filed: Sep. 23, 2020

(65) Prior Publication Data
US 2021/0046299 A1 Feb. 18, 2021

Related U.S. Application Data

(63) Continuation of application No. 16/040,892, filed on Jul. 20, 2018, now Pat. No. 10,806,914, which is a
(Continued)

(51) Int. Cl.
*A61M 37/00* (2006.01)
*A61B 17/20* (2006.01)
(Continued)

(52) U.S. Cl.
CPC ....... *A61M 37/0015* (2013.01); *A61B 17/205* (2013.01); *A61K 9/0021* (2013.01);
(Continued)

(58) Field of Classification Search
CPC ...... A61M 37/0015; A61M 2037/0023; A61M 2037/003; A61M 2037/0038;
(Continued)

(56) References Cited

U.S. PATENT DOCUMENTS 3,797,494 A 3/1974 Zaffaroni
3,964,482 A 6/1976 Gerstel
(Continued)

FOREIGN PATENT DOCUMENTS

EP 2100850 A1 9/2009
WO 1999045860 A1 9/1999
(Continued)

OTHER PUBLICATIONS

Madara, JL, "Regulation of the movement of solutes across tight junctions", Annu Rev Physiol, 1998, 60:143-59.
(Continued)

*Primary Examiner* — Amber R Stiles
(74) *Attorney, Agent, or Firm* — PROCOPIO, CORY, HARGREAVES & SAVITCH LLP

(57) ABSTRACT

Disclosed are composite microneedles arrays including microneedles and a film overlaying the microneedles. The film includes a plurality of nano-sized structures fabricated thereon. Devices may be utilized for interacting with a component of the dermal connective tissue. A random or non-random pattern of structures may be fabricated such as a complex pattern including structures of differing sizes and/or shapes. Devices may be beneficially utilized for delivery of an agent to a cell or tissue. Devices may be utilized to directly or indirectly alter cell behavior through the interaction of a fabricated nanotopography with the plasma membrane of a cell and/or with an extracellular matrix component.

8 Claims, 22 Drawing Sheets

Related U.S. Application Data continuation of application No. 15/382,774, filed on Dec. 19, 2016, now Pat. No. 10,029,084, which is a continuation of application No. 13/641,504, filed as application No. PCT/IB2011/051864 on Apr. 27, 2011, now Pat. No. 9,526,883.

(60) Provisional application No. 61/435,939, filed on Jan. 25, 2011, provisional application No. 61/411,071, filed on Nov. 8, 2010, provisional application No. 61/328,723, filed on Apr. 28, 2010.

(51) Int. Cl.
| | |
|---|---|
| *A61K 9/00* | (2006.01) |
| *A61K 9/70* | (2006.01) |
| *A61K 38/17* | (2006.01) |
| *A61K 38/19* | (2006.01) |
| *B29C 59/00* | (2006.01) |
| *B29C 59/02* | (2006.01) |
| *B29L 31/00* | (2006.01) |

(52) U.S. Cl.
CPC ........ *A61K 9/7023* (2013.01); *A61K 38/1793* (2013.01); *A61K 38/191* (2013.01); *B29C 59/002* (2013.01); *B29C 59/026* (2013.01); *A61M 2037/0023* (2013.01); *A61M 2037/003* (2013.01); *A61M 2037/0038* (2013.01); *A61M 2037/0053* (2013.01); *A61M 2037/0061* (2013.01); *B29C 2059/023* (2013.01); *B29K 2995/0056* (2013.01); *B29L 2031/7544* (2013.01); *B29L 2031/756* (2013.01); *Y10T 156/10* (2015.01); *Y10T 156/1039* (2015.01); *Y10T 156/1057* (2015.01)

(58) Field of Classification Search
CPC .. A61M 2037/0053; A61M 2037/0061; A61M 37/00; A61M 5/158; A61B 17/205; A61K 9/0021; A61K 9/7023; A61K 38/1793; A61K 38/191; B29C 59/002; B29C 59/026; B29C 2059/023; B29K 2995/0056; B29L 2031/7544; B29L 2031/756; Y10T 156/10; Y10T 156/1039; Y10T 156/1057; A61P 37/06
See application file for complete search history.

(56) References Cited

U.S. PATENT DOCUMENTS

| | | | |
|---|---|---|---|
| 4,031,894 A | 6/1977 | Urquhart |
| 4,051,840 A | 10/1977 | Kantrowitz |
| 4,201,211 A | 5/1980 | Chandrasekaran |
| 4,379,454 A | 4/1983 | Campbell |
| 4,436,741 A | 3/1984 | Urquhart |
| 4,588,580 A | 5/1986 | Gale |
| 4,615,699 A | 10/1986 | Gale |
| 4,661,105 A | 4/1987 | Gale |
| 4,681,584 A | 7/1987 | Gale |
| 4,698,062 A | 10/1987 | Gale |
| 4,725,272 A | 2/1988 | Gale |
| 4,832,953 A | 5/1989 | Campbell |
| 4,880,633 A | 11/1989 | Loper |
| 4,908,027 A | 3/1990 | Enscore |
| 5,004,610 A | 4/1991 | Osborne |
| 5,310,559 A | 5/1994 | Shah |
| 5,328,470 A | 7/1994 | Nabel |
| 5,342,623 A | 8/1994 | Enscore |
| 5,344,656 A | 9/1994 | Enscore |
| 5,364,630 A | 11/1994 | Osborne |
| 6,132,755 A | 10/2000 | Eicher |
| 6,312,612 B1 | 11/2001 | Sherman et al. |
| 6,334,856 B1 | 1/2002 | Allen |
| 6,375,978 B1 | 4/2002 | Kleiner |
| 6,471,993 B1 | 10/2002 | Shastri |
| 6,561,143 B2 | 5/2003 | Holtzman |
| 6,569,143 B2 | 5/2003 | Alchas |
| 6,591,124 B2 | 7/2003 | Sherman et al. |
| 6,611,707 B1 | 8/2003 | Prausnitz et al. |
| 6,656,147 B1 | 12/2003 | Gertsek |
| 6,663,820 B2 | 12/2003 | Arias |
| 6,767,341 B2 | 7/2004 | Cho |
| 6,881,203 B2 | 4/2005 | Delmore |
| 6,908,453 B2 | 6/2005 | Fleming et al. |
| 6,923,930 B2 | 8/2005 | Ling et al. |
| 6,926,953 B2 | 8/2005 | Nealey |
| 6,979,347 B1 | 12/2005 | Wu |
| 6,980,855 B2 | 12/2005 | Cho |
| 6,995,336 B2 | 2/2006 | Hunt |
| 7,022,465 B2 | 4/2006 | Heidari |
| 7,041,228 B2 | 5/2006 | Heidari |
| 7,048,723 B1 | 5/2006 | Frazier |
| 7,108,681 B2 | 9/2006 | Gartstein |
| 7,115,108 B2 | 10/2006 | Wilkinson |
| 7,129,554 B2 | 10/2006 | Lieber |
| 7,131,987 B2 | 11/2006 | Sherman |
| 7,137,336 B2 | 11/2006 | Heidari et al. |
| 7,185,663 B2 | 3/2007 | Koch |
| 7,189,435 B2 | 3/2007 | Tuominen |
| 7,195,734 B2 | 3/2007 | Heidari |
| 7,226,439 B2 | 6/2007 | Prausnitz |
| 7,250,037 B2 | 7/2007 | Shermer |
| 7,252,492 B2 | 8/2007 | Olsson et al. |
| 7,285,113 B2 | 10/2007 | Yeshurun |
| 7,315,758 B2 | 1/2008 | Kwiatkowski |
| 7,332,339 B2 | 2/2008 | Canham |
| 7,364,568 B2 | 4/2008 | Angel et al. |
| 7,374,864 B2 | 5/2008 | Guo |
| 7,410,476 B2 | 8/2008 | Wilkinson et al. |
| 7,416,541 B2 | 8/2008 | Yuzhakov |
| 7,429,258 B2 | 9/2008 | Angel |
| 7,449,200 B2 | 11/2008 | Sung |
| 7,473,244 B2 | 1/2009 | Frazier et al. |
| 7,531,120 B2 | 5/2009 | Van Rijn et al. |
| 7,537,590 B2 | 5/2009 | Santini, Jr. |
| 7,544,770 B2 | 6/2009 | Haynie |
| 7,556,615 B2 | 7/2009 | Pettis |
| 7,563,451 B2 | 7/2009 | Lin |
| 7,572,405 B2 | 8/2009 | Sherman |
| 7,578,954 B2 | 8/2009 | Gartstein |
| 7,582,069 B2 | 9/2009 | Laurent |
| 7,588,552 B2 | 9/2009 | Yeshurun |
| 7,611,481 B2 | 11/2009 | Cleary |
| 7,627,938 B2 | 12/2009 | Kim |
| 7,651,475 B2 | 1/2010 | Angel et al. |
| 7,658,728 B2 | 2/2010 | Yuzhakov |
| 7,670,127 B2 | 3/2010 | Heidari |
| 7,670,452 B2 | 3/2010 | Heidari et al. |
| 7,687,007 B2 | 3/2010 | Ling et al. |
| 7,704,425 B2 | 4/2010 | Heidari et al. |
| 7,717,693 B2 | 5/2010 | Keil et al. |
| 7,753,888 B2 | 7/2010 | Mukerjee |
| 7,754,131 B2 | 7/2010 | Olsson et al. |
| 7,785,301 B2 | 8/2010 | Yuzhakov |
| 7,803,574 B2 | 9/2010 | Desai |
| 7,828,827 B2 | 11/2010 | Gartstein |
| 7,846,488 B2 | 12/2010 | Johnson |
| 7,855,046 B2 | 12/2010 | Suleski |
| 7,862,849 B2 | 1/2011 | Stellacci et al. |
| 7,901,387 B2 | 3/2011 | Stemme |
| 7,914,480 B2 | 3/2011 | Cleary |
| 7,914,813 B2 | 3/2011 | Adachi |
| 7,918,814 B2 | 4/2011 | Prausnitz et al. |
| 7,972,616 B2 | 7/2011 | Dubrow |
| 7,981,346 B2 | 7/2011 | Griss |
| 7,997,274 B2 | 8/2011 | Baska |
| 8,052,633 B2 | 11/2011 | Kendall |
| 8,057,842 B2 | 11/2011 | Choi |
| 8,088,321 B2 | 1/2012 | Ferguson et al. |
| 8,097,456 B2 | 1/2012 | Borenstein et al. |
| 8,118,753 B2 | 2/2012 | Cho et al. |
| 8,137,697 B1 | 3/2012 | Sung |

(56) References Cited

U.S. PATENT DOCUMENTS

| | | |
|---|---|---|
| 8,137,736 B2 | 3/2012 | Zhu |
| 8,162,901 B2 | 4/2012 | Gonnelli et al. |
| 8,238,995 B2 | 8/2012 | Chandrasekaran |
| 8,366,677 B2 | 2/2013 | Kaspar |
| 8,389,205 B2 | 3/2013 | Duerig |
| 8,419,708 B2 | 4/2013 | Tokumoto |
| 8,506,530 B2 | 8/2013 | Laermer |
| 8,574,615 B2 | 11/2013 | Tenney |
| 8,690,838 B2 | 4/2014 | Ozawa |
| 8,696,637 B2 | 4/2014 | Ross |
| 8,915,957 B2 | 12/2014 | Arney |
| 8,944,804 B2 | 2/2015 | Robeson |
| 9,028,409 B2 | 5/2015 | Yodfat et al. |
| 9,522,262 B2 * | 12/2016 | Ross ............... C12N 15/113 |
| 9,522,263 B2 * | 12/2016 | Ross ............... A61M 37/0015 |
| 9,526,883 B2 * | 12/2016 | Ross ............... A61K 38/1793 |
| 9,545,507 B2 | 1/2017 | Ross |
| 9,550,053 B2 * | 1/2017 | Ross ............... A61M 37/0015 |
| 10,029,082 B2 * | 7/2018 | Ross ............... A61P 19/02 |
| 10,029,083 B2 * | 7/2018 | Ross ............... C12N 15/89 |
| 10,029,084 B2 * | 7/2018 | Ross ............... A61K 38/1793 |
| 10,213,588 B2 * | 2/2019 | Ross ............... A61K 31/70 |
| 10,806,914 B2 * | 10/2020 | Ross ............... A61K 9/7023 |
| 2002/0082543 A1 | 6/2002 | Park |
| 2002/0133129 A1 | 9/2002 | Arias |
| 2002/0183688 A1 | 12/2002 | Lastovich |
| 2003/0045837 A1 | 3/2003 | Delmore et al. |
| 2004/0028875 A1 | 2/2004 | Van Rijn |
| 2004/0063100 A1 | 4/2004 | Wang |
| 2004/0087992 A1 | 5/2004 | Gartstein |
| 2004/0106904 A1 | 6/2004 | Gonnelli |
| 2005/0049625 A1 | 3/2005 | Shaya |
| 2005/0112135 A1 | 5/2005 | Cormier |
| 2005/0118388 A1 | 6/2005 | Kingsford |
| 2005/0119723 A1 | 6/2005 | Peacock |
| 2005/0124967 A1 | 6/2005 | Kaestner |
| 2005/0137531 A1 | 6/2005 | Prausnitz |
| 2005/0143713 A1 | 6/2005 | Delmore |
| 2005/0178760 A1 | 8/2005 | Chan |
| 2005/0187521 A1 | 8/2005 | Fleming et al. |
| 2005/0203613 A1 | 9/2005 | Arney et al. |
| 2006/0024358 A1 | 2/2006 | Santini |
| 2006/0025848 A1 | 2/2006 | Weber |
| 2006/0051404 A1 | 3/2006 | Yeshurun |
| 2006/0204738 A1 | 9/2006 | Dubrow et al. |
| 2006/0264893 A1 | 11/2006 | Sage, Jr. |
| 2007/0066934 A1 | 3/2007 | Etheredge |
| 2007/0078376 A1 | 4/2007 | Smith |
| 2007/0081977 A1 | 4/2007 | Horstmann |
| 2007/0088248 A1 | 4/2007 | Glenn |
| 2007/0110810 A1 | 5/2007 | Smith |
| 2007/0112309 A1 | 5/2007 | Zucker |
| 2007/0112548 A1 | 5/2007 | Dickerson |
| 2007/0191761 A1 | 8/2007 | Boone |
| 2007/0249552 A1 | 10/2007 | Khalili |
| 2007/0250018 A1 | 10/2007 | Adachi |
| 2007/0260201 A1 | 11/2007 | Prausnitz |
| 2007/0282247 A1 | 12/2007 | Desai et al. |
| 2008/0026464 A1 | 1/2008 | Borenstein |
| 2008/0088066 A1 | 4/2008 | Ferguson |
| 2008/0091226 A1 | 4/2008 | Yeshurun |
| 2008/0097352 A1 | 4/2008 | Beck |
| 2008/0108958 A1 | 5/2008 | Carter |
| 2008/0167601 A1 | 7/2008 | Laermer et al. |
| 2008/0200883 A1 | 8/2008 | Tomono |
| 2008/0217180 A1 | 9/2008 | Doye |
| 2008/0221408 A1 | 9/2008 | Hoarau |
| 2008/0262416 A1 | 10/2008 | Duan |
| 2008/0269666 A1 | 10/2008 | Wang |
| 2008/0269685 A1 | 10/2008 | Singh |
| 2008/0305989 A1 | 12/2008 | Wen |
| 2008/0311172 A1 | 12/2008 | Schapira |
| 2008/0312610 A1 | 12/2008 | Binks |
| 2009/0012494 A1 | 1/2009 | Yeshurun |
| 2009/0043279 A1 | 2/2009 | Kaspar |
| 2009/0069788 A1 | 3/2009 | Yeshurun |
| 2009/0093776 A1 | 4/2009 | Yue |
| 2009/0093879 A1 | 4/2009 | Wawro |
| 2009/0099427 A1 | 4/2009 | Jina et al. |
| 2009/0099502 A1 | 4/2009 | Tokumoto |
| 2009/0099537 A1 | 4/2009 | Devoe et al. |
| 2009/0118662 A1 | 5/2009 | Schnall |
| 2009/0118672 A1 | 5/2009 | Gonnelli |
| 2009/0137926 A1 | 5/2009 | Srinivasan |
| 2009/0177273 A1 | 7/2009 | Piveteau |
| 2009/0187167 A1 | 7/2009 | Sexton |
| 2009/0198189 A1 | 8/2009 | Simons |
| 2009/0232870 A1 | 9/2009 | Srivastava |
| 2009/0234301 A1 | 9/2009 | Tomono |
| 2010/0004733 A1 | 1/2010 | Atanasoska |
| 2010/0021464 A1 | 1/2010 | Archambeau |
| 2010/0028604 A1 | 2/2010 | Bhushan et al. |
| 2010/0076035 A1 | 3/2010 | Carter |
| 2010/0121307 A1 | 5/2010 | Lockard |
| 2010/0168506 A1 | 7/2010 | Moon |
| 2010/0215580 A1 | 8/2010 | Hanes |
| 2010/0256568 A1 | 10/2010 | Frederickson |
| 2010/0274203 A1 | 10/2010 | Lee |
| 2010/0316960 A1 | 12/2010 | Duerig et al. |
| 2011/0021996 A1 | 1/2011 | Lee |
| 2011/0046557 A1 | 2/2011 | Lee |
| 2011/0059150 A1 | 3/2011 | Kendall et al. |
| 2011/0144591 A1 | 6/2011 | Ross |
| 2011/0160069 A1 | 6/2011 | Corrie |
| 2011/0270221 A1 | 11/2011 | Ross |
| 2011/0276003 A1 | 11/2011 | Luttge |
| 2012/0089117 A1 | 4/2012 | Junginger |
| 2012/0109065 A1 | 5/2012 | Backes |
| 2012/0114734 A1 | 5/2012 | Desai et al. |
| 2012/0128932 A1 | 5/2012 | Veith |
| 2013/0144217 A1 | 6/2013 | Ross |
| 2013/0144257 A1 | 6/2013 | Ross |
| 2013/0150822 A1 | 6/2013 | Ross |
| 2013/0158505 A1 | 6/2013 | Ross |
| 2013/0211310 A1 * | 8/2013 | Bommarito ............ B08B 17/06 428/141 |
| 2013/0331792 A1 | 12/2013 | Karp |
| 2014/0112921 A1 | 4/2014 | Ross |
| 2014/0287019 A1 | 9/2014 | Ollerenshaw |
| 2014/0343532 A1 | 11/2014 | Ross |
| 2017/0157380 A1 | 6/2017 | Ross |
| 2017/0157381 A1 | 6/2017 | Ross |

FOREIGN PATENT DOCUMENTS

| | | |
|---|---|---|
| WO | 2000074764 A1 | 12/2000 |
| WO | 2001075164 A2 | 10/2001 |
| WO | 2002030506 A2 | 4/2002 |
| WO | 2002032480 A2 | 4/2002 |
| WO | 2003020359 A2 | 3/2003 |
| WO | 2003024508 A2 | 3/2003 |
| WO | 2003092785 A1 | 11/2003 |
| WO | 2005049128 A1 | 6/2005 |
| WO | 2006062974 A2 | 6/2006 |
| WO | 2006075689 A1 | 7/2006 |
| WO | 2007012114 A1 | 2/2007 |
| WO | 2007070004 A2 | 6/2007 |
| WO | 2007081876 A2 | 7/2007 |
| WO | 2007112309 A2 | 10/2007 |
| WO | 2008003564 A1 | 1/2008 |
| WO | 2008024141 A2 | 2/2008 |
| WO | 2009079589 A2 | 6/2009 |
| WO | 2009113856 A1 | 9/2009 |
| WO | 2010070628 A1 | 6/2010 |
| WO | 2010087971 A2 | 8/2010 |
| WO | 2010126640 A2 | 11/2010 |
| WO | 2011116388 A1 | 9/2011 |
| WO | 2011135531 A2 | 11/2011 |

(56) References Cited

FOREIGN PATENT DOCUMENTS

| WO | 2012006677 A1 | 1/2012 |
|---|---|---|
| WO | 2012046149 A1 | 4/2012 |

OTHER PUBLICATIONS

Martinez-Palomo et al., "Experitnental Modulation of Occluding Junctions in a Cultured Transporting Epithelium", J. Cell Biology, 1980, 87: 736-745.
Ojakian, GK, "Tumor promotor-induced changes in the permeability of epithelial cell tight junctions", Cell, 1981, 23(1): 95-103.
Rubin, LL, "Endothelial cells: adhesion and tight junctions", Curr Opin Cell Biol, 1992, 4(5):830-3.
Verma et al., "Development of Transdermal Drug Dosage Fomulation for the Anti-Rheumatic Ayurvedic Medicianal Plants", Ancient Sci. Life, 2007; 11:66-9.
Ahmed et al.; "Bis (diacetylene)s I: Langmuir-Blodgett films", Thin Solid Films 198: 141-153; 1990.
Citi, S., "Protein Kinase Inhibitors Prevent Junction Dissociation Induced by Low Extracellular Calcium in MDCK Epithelial Cells", J Cell Biology, 1992, 117(1) 169-178.
Geiger & Ayalon, "Cadherins", Annu Rev Cell Biol, 1992, 8:307-32.
Gumbiner & Simons, "A Functional Assay for Proteins Involved in Establishing an Epithelial Occluding Barrier: Identification of an Uvomorulin-like Polypetide", J. Cell Biology, 1986, 102: 457-468.
Hirano et al., "Calcium-dependent Cell-Cel Adhesion Molecules (Cadherins): Subclass Specificities and Possible Involvement of Actin Bundles" J. Cell Biology, 1987, 105(6): 2501-2510.
Kaushal et al., Influence of Piperline on Transcutaneous Permeation of Repaglinide in Rats and on Tight Junction Proteins in HaCaT Cells: Unveiling the Mechanisms for Enhanced Permeation; Sci. Pharm. 2009; 77: 877-897.
Kitner, C., "Regulation of embryonic cell adhesion by the cadherin cytoplasmic domain", Cell, 1992, 69(2): 225-36.
Korhonen et al., "Nitric oxide production and signaling in inflammation", Curr Drug Targets Inflamm Allergy 4(4): 471-9, 2005.
Langeler et al., "Norepinephrine and iloprost improve barrier function of human endothelial cellmonolayers: role of cAMP", Am J Physio Cell Physiol, 1991, vol. 260(5), C1052-C1059.
Nagafuchi & Takechi, "Cell binding function of E-cadherin is regulated by the cytoplasmic domain", EMBO Journal, 1988, 7(12): 3679-3684.
Ozawa et al., "The cytoplasmic domain of the cell adhesion molecule uvomorulin associates with three independent proteins structurally related in different species", EMBO Journal, 1989, 8(6): 1711-1717.
Ozawa et al., "Uvomorulin-catenin complex formation is regulated by a specific domain in the cytoplasmic region of the cell adhesion molecule", Dev Biology, 1990, 87: 4246-4250.
Rubin et al., "A Cell Culture Model of the Blood-Brain Barrier", J. Cell Biology, 1991, 115: 1725-1735.
Rutten et al., "Electrical resistance and macromolecular permeability of brain endothelial monolayer cultures", Brain Res, 1987, 425(2): 301-10.
Schubert et al, "Sliding-induced adhesion of stiff polymer microfibre arrays. II, Microscale behavior", J Royal Society; Jan. 2008, 5. 845-853.
Stappert et al., "A short core region of E-cadherin is essential for certain binding and is highly phosphorylated", 1993, Cell Ahdes Commun. 2(4): 319-27.
Stelzner et al., "Role of cyclic adenosine monophosphate in the induction of endothelial barrier properties", J. Cell Physiol. 1989, 139(1): 157-66.
Abstract of Japanese Patent—JP2001238964, Sep. 4, 2001, 1 page.
Abstract of Japanese Patent—JP2008511382, Apr. 17, 2008, 2 pages.

Ainslie, Kristy M., and Tejal A. Desai. "Microfabricated implants for applications in therapeutic delivery, tissue engineering, and biosensing." Royal Society of Chemistry. 8. (2008): 1864-1878.
Ainslie, Kristy M., Rachel D. Lowe, Tristan T. Beaudette, Lamar Petty, Eric M. Bachelder, and Tejal A. Desai. "Microfabricated Devices for Enhanced Bioadhesive Drug Delivery: Attachment to and Small-Molecule Release Through a Cell Monolayer Under Flow." Small. (2009).
Bekarde, Iil Gercek. "Biomimetic Apatite-coated PCL Scaffolds: Effect of Surface Nanotopography on Cellular Functions." Journal of Bioactive and Compatible Polymers. 24.6 (2009): 507-524.
Berry, C.C., M.J. Dalby, R.O.C. Oreffo, D. McCloy, and S. Affrosman. "The interaction of human bone marrow cells with nanotopographical features in three dimensional constructs." Journal of Biomedical Materials Research Part A. 79A.2 (2006): 431-439.
Biehl, Jesse K., Satoshi Yamanaka, Tejal A, Desai, Keneth R. Boheler, and Brenda Russell. "Proliferation of Mouse Embryonic Stem Cell Progeny and the Spontaneous Contractile Activity of Cardiomyocytes Are Affected by Microtopography." Developmental Dynamics. 238. (2009): 1964-1973.
Brunauer, Stephen, P.H. Emmett, and Edward Tellet. "Adsorption of Gases in Multimolecular Layers." Journal of the American Chemical Society. 60. (1938): 309-319.
Chandler, David L.. "PhysOrg.com." Harnessing nanopatterns: Tiny textures can produce big differences. N.p., Sep. 24, 2009. Web. Dec. 1, 2009. <http://www.physorg.com/news173004362.html>.
Choi, Chang-Hwan, Sepideh H. Hagvall, Bengamin M. Wu, James C.Y. Dunn, Ramin E. Beygui, and Chang-Jin "CJ" Kim. "cell interaction with three-dimensional sharp-tip nanotopography." Biomaterials. 28.9 (2007): 1672-1679.
Chun, YW, D Khang, KM Haberstroh, and TJ Webster. "The role of polymer nanosurucace roughness and the submicron pores in improving bladder urothelial cell density and inhibiting calcium oxalate stone formation." Nanotechnology. 20.8 (2009): 85104.
Cohn, Abby. "Drug Delivery, Nanoscale." Innovations. 3.4 (2009).
Curtis, Adam SG, Matthew Dalby, and Nikolaj Gadegaard. "Cell signaling arising from nanotopography: implicatinos for nanomedicaldevices." Nanomedicine. 1.1 (2006): 67-72.
Dalby, Matthew J. "Nanostructured surfaces: cell engineering and cell biology." Nanomedicine. 4.3 (2009): 247-248.
Dalby, Matthew J., Catherine C. Berry, Mathis O. Riehle, Doncan S. Sutherland, Hossein Agheli, and Adam S.G. Curtis. "Attempted endocytosis of nano-environment produced by colloidal lithography by human fibroblasts." Experimental Cell Research. 295. (2004): 387-394.
Dalby, Matthew J., Mathis Riehle, Duncan Sutherland, Hossein Agheli, and Adam S.G. Curtis. "Nano-Topography Induces Mechanotransduction in Human Fibroblasts." European Cells and Materials. 6.2 (2003): 31.
Dalby, Matthew J., Stephen J. Yarwood, Mathis O. Riehle, Heather J.H. Johnstone, Stanley Affrossman, and Adam S.G. Curtis. "Increasing Fibroblast Response to Materials Using Nanotopography: Morphological and Genetic measurements of Cell Response to 13-nm-High Polymer Demixed Islands." Experimental Cell Research. 276.1 (2002): 1-9.
Fischer, Kathleen E., Benjamin J. Aleman, Sarah L. Tao, R. Hugh Daniels, Esther M. Li, Mark D. Bunger, Ganesh Nagaraj, Parminder Singh, et al. "Biomimetic Nanowire Coatings for Next Generation Adhesive Drug Delivery Systems." Nano Letters. 9.2 (2009): 716-720.
Hart, A, N Gadegaard, C.D.W. Wilkinson, R.O.C Oreffo, and M.J. Dalby. "Filapodial Sensing of Nanotopography in Osteoprogenitor Cells." European Cells and Materials. 10.2 (2005): 65.
He, et al., "The anatase phase of nanotopography titania plays an important role on osteoblast cell morphology and proliferation", Journal of Mater. Sci: Mater Med (2008), 19:3465-3472.
Hu, Wenchuang, Fern Yoon, Adam Crouch, Li Tao, Heather Hillebrenner, Jagadeesh Setti Guthi, Moon Kim, and Jinming Gao. "Surface Energy Induced Patterning of Polymer Nanostructures for Cancer Diagnosis and Therapy." IEEE Nano 2007 Conference Paper. (2007).
Lim, Jung Yul, Joshua C Hansen, Christopher A Siedlecki, James Runt, and Henry J Donahue. "Human foetal osteoblastic cell

(56) References Cited

OTHER PUBLICATIONS response to polymer-demixed nanotopographic interfaces." Journal of the Royal Society Interface. 2.2 (2005): 97-108.

Mandavi, Alborz, Lino Ferreira, Cathryn Sundback, et al. "A biodegradable and biocompatible gecko-inspired tissue adhesive." PNAS. 105.7 (2008): 2307-2312.

Abstract—Meirelles, L, F Currie, M Jacobsson, T Albrektsson, and A Wennerberg. "The effect of chemical and nanotopographical modifications on the early stages of osseointegration." International Journal of Oral and Maxillofacial Implants. 23.4 (2008): 641-647.

Abstract—Mendelsohn, Adam, and Tejal Desai. "Inorganic Nanoporous Membranes for Immunoisolated Cell-Based Drug Delivery." Therapeutic Applications of Cell Microencapsulation, (2010).

Ng, C.K.M., W.L. Poon, W.Y. Li, T. Cheung, S.H. Cheng, and K.N. Yu. "Study of substrate topographical effects on epithelial cell behavior using etched alpha-particle tracks on PADC films." Nuclear Instruments and Methods in Physics Research Section B: Beam Interactions with Materials and Atoms. 266.14 (2008): 3247-3256.

Orr, Galya, David J. Panther, Jaclyn L. Phillips, Barbara J. Tarasevich, Alice Dohnalkova, Justin G. Teeguarden, and Joel G. Pounds. "Submicrometer and Nanoscale Inorganic Particles Exploit the Actin Machinery to Be Propelled along Microvilli-likestructures into Alveolar Cells." American Chemical Society Nano. 1.5 (2007): 463-475.

Peng, Lily, Adam D. Mendelsohn, Thomas J. LaTempa, Sorachon Yoriya, Craig A. Grimes, and Tejal A. Desai. "Long-Term Small Molecule and Protein Elution from TiO2 Nanotubes." Nano Letters. 9.5 (2009): 1932-1936.

Peng, Lily, Matthew G. Eltgroth, Thomas J. Latempa, Craig A. Grimes, and Tejal A. Desai. "The effect of TiO2 nanotubes on endothelial function and smooth muscle proliferation." Journal of Biomaterials. 30. (2009): 1268-1272.

Sapra, Bharti, Subheet Jain, and A.K. Tiwary. "Transdermal Delivery of Carvedilol Containing Glycyrrhizin and Chitosan as Permeation Enhancers:Biochemical, Biophysical, Microscopic and Pharmacodynamic Evaluation." Drug Delivery. 15.7 (2008): 443-454.

Abstract—Sapra, Bharti, Subheet Jain, and A.K. Tiwary. "Transdermal delivery of carvedilol in rats:probing the percutaneous permeation enhancement mechanism of soybean extract-chitosan mixture." Drug Delivery. 35.10 (2009): 1230-1241.

Sapra, Bharti, Subheet Jain, and Ashok K. Tiwary. "Effect of Asparagus racemous Extract on Transdermal Delivery of Carvedilol: A Mechanistic Study." American Association of Pharmaceutical Scientists PharmSciTech. 10.1 (2009): 199.

Teo, Benjamin KK, et al. "The effect of micro and nanotopography on endocytosis in drug and gene delivery systems", Biomaterials, 32 (2011), 9866-9875.

Thakar, Rahul G., Matthew G. Chown, Anuj Patel, Lily Peng, Sanjay Kumar, and Tejal A. Desai. "Contractility-Dependent Modulation of Cell Proliferation and Adhesion by Microscale Topographical Cues." Small. 4.9 (2008): 1416-1424.

Valenta, Claudia, and Barbara G. Auner. "The use of polymers for dermal and transdermal delivery." European Journal of Pharmaceutics and Biopharmaceutics. 58.2 (2004): 279-289.

Wang, Min, and Yan Lu. "Nano patterned PDMS for periodontal ligament fibroblast culture." Surface and Coatings Technology. 204.4 (2009): 525-530.

Wei, Song, and Chen Hong. "Protein adsorption on materials surfaces with nano-topography." Chinese Science Bulletin. 52.23 (2007): 3169-3173.

Wood, M.A. "Colloidal lithography and current fabrication techniques producing in-plane nanotopography for biological applications." Journal of the Royal Society Interface. 4.12 (2007): 1-17.

Abstract—Yao, Chang, and Thomas J Webster. "Nano-Surface Modification on Titanium Implants for Drug Delivery." Materials Research Society. (2007).

Yim, Evelyn K.F., Ron M. Reano, Stella w. Pang, Albert F. Yee, Christopher S. Chen, and Kam W. Leong. "Nanopattern-induced changes in morphology and motility of smooth muscle cells." Journal of Biomaterials. 58.1 (2005).

The Journal of American Chem. Soc., vol. LX, Jan.-Jun. 1938.

Abstract of Japanese Patent—JP2008237673, dated Oct. 9, 2008, 1 page.

Abstract of Japanese Patent—JP2009207733, dated Sep. 17, 2009, 1 page.

Abstract of Japanese Patent—JPH08337521, dated Dec. 24, 1996, 2 pages.

Inkyu Park et al., Towards the silicon nanowire-based sensor for intracellular biochemical detection, 6 pages, Apr. 1, 2007, Biosensors and Bioelectronics, vol. 22, No. 9-10.

Supplementary European Search Report dated Sep. 9, 2013, 12 pages.

Al-Qallaf et al., "Optimizing Microneedle Arrays to Increase Skin Permeability for Transdermal Drug Delivery," Interdisciplinary Transport Phenomena V: Ann. N.Y. Acad. Sci., 2009, pp. 1-12.

Abstract of Japanese Patent—JP2001238964, dated Sep. 4, 2001, 1 page.

Abstract of Japanese Patent—JP2008511382, dated Apr. 17, 2008, 2 pages.

Berliner et al., "Impact of Transdermal Fentanyl on Quality of Life in Rheumatoid Arthritis", Clinical Journal of Pain, 2007, 23(6): 530-534.

Biggs et al., "Interactions with Nanoscale Topography: Adhesion quantification and signal transduction in cells of osteogenic and multipotent lineage," Journal of Biomedical Materials Research Part A, 2008, pp. 195-208.

Kumar et al. "Transdermal Drug Delivery System: An Overview," International Journal of Pharmaceutical Sciences Review and Research. 3.2 (2010): 49-54.

Communication Pursuant to Article 94(3) EPC dated Mar. 11, 2024, for EP Application 11 830 267.8-1113, 4 pages.

* cited by examiner square packing hexagonal packing

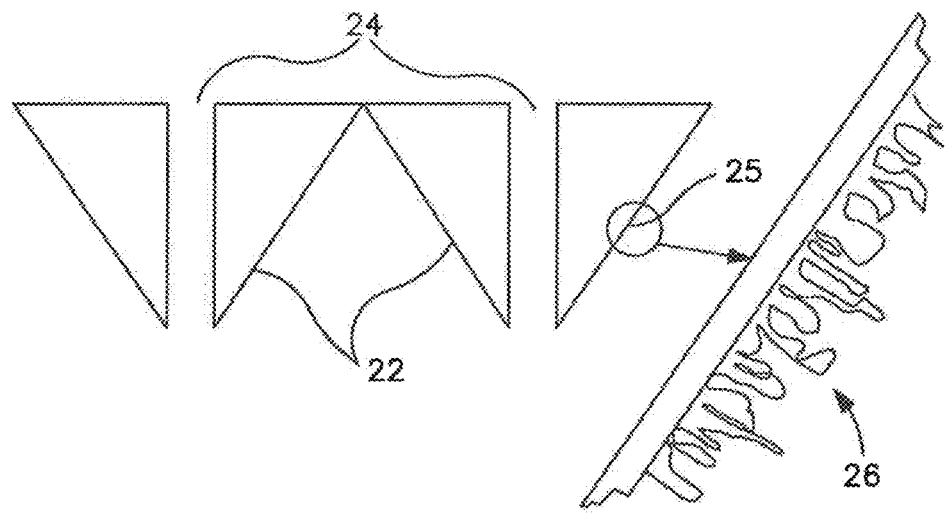
FIG. 12
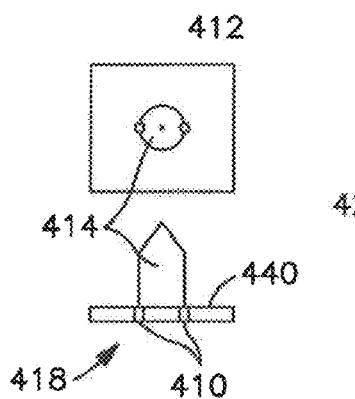 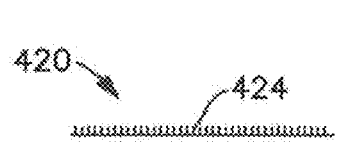 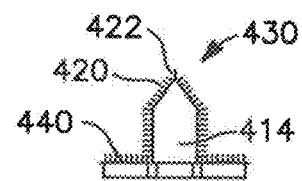
FIG. 13A  FIG. 13B  FIG. 13C

DN1

Hole depth=500nm

DN2

Hole depth=500nm

DN3

Hole depth=500nm

DN4

Hole depth=400–500nm
(Random Variation)

FIG. 27E
NTTAT2
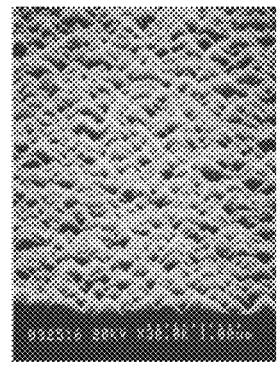
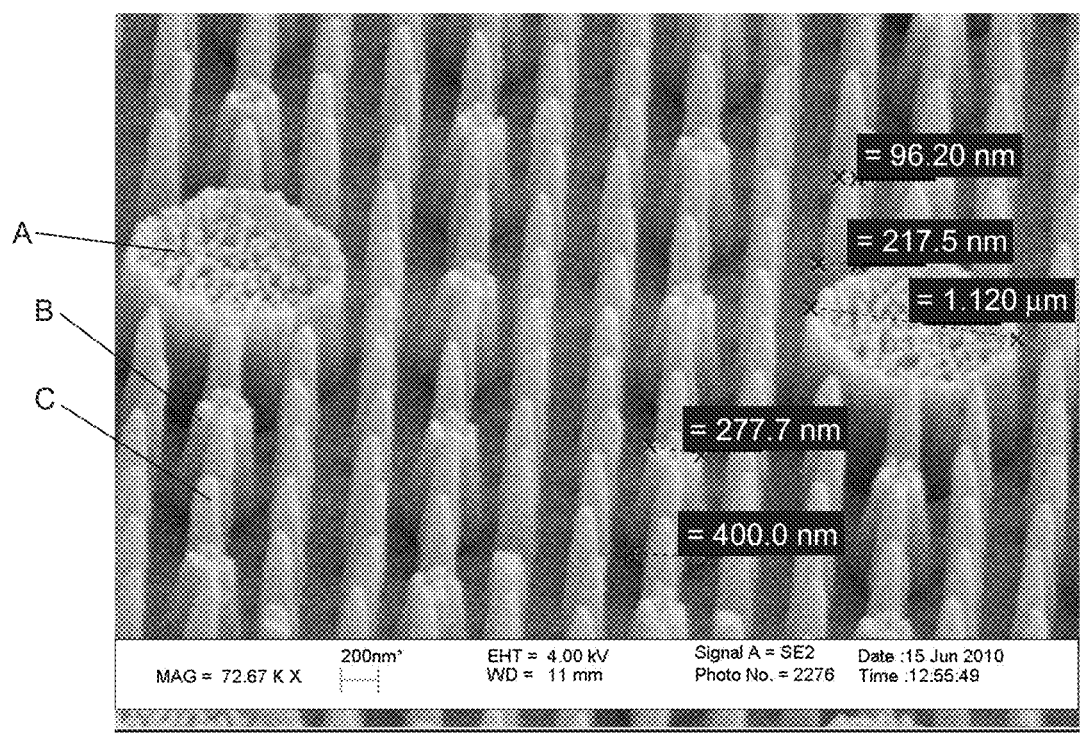
FIG. 28

COMPOSITE MICRONEEDLE ARRAY INCLUDING NANOSTRUCTURES THEREON

CROSS REFERENCE TO RELATED APPLICATIONS

This application is a continuation of U.S. application Ser. No. 16/040,892, having a filing date of Jul. 20, 2018, which is a continuation of U.S. application Ser. No. 15/382,774 having a filing date of Dec. 19, 2016, which is a continuation of U.S. application Ser. No. 13/641,504 having a filing date of Feb. 22, 2013, which claims priority to International Patent Application No. PCT/B2011/051864 having a filing date of Apr. 27, 2011, U.S. Provisional Patent Application Ser. No. 61/328,723 having a filing date of Apr. 28, 2010, U.S. Provisional Patent Application Ser. No. 61/411,071 having a filing date of Nov. 8, 2010, and U.S. Provisional Patent Application Ser. No. 61/535,939 having a filing date of Jan. 25, 2011, all of which are incorporated herein in their entirety by reference.

BACKGROUND

Primary drug delivery methods include oral delivery and injections, but these methods present difficulties. For instance, injections are painful and both methods tend to provide bursts of agents rather than a preferred steady-state delivery. Additionally, the successful long term use of both oral delivery and injected delivery requires the patient to consistently meet the time requirements for the delivery method.

Transdermal delivery materials have been developed in an attempt to provide a painless route for delivery of active agents over a sustained period with little or no interruption of the patient's daily routine. Unfortunately, natural dermal characteristics such as the overlapping corneocytes of the stratum corneum, the tight junction of the stratum *granulosum*, and Langerhans cells of the stratum *spinosum* that may institute an immune response and/or a foreign body response all present barriers to successful transdermal delivery of an active agent.

Devices including microneedles that may facilitate transdermal delivery of active agents have improved transdermal delivery. A microneedle transdermal device includes an array of needles that may penetrate at least the stratum corneum of the skin and reach an underlying layer of the skin. In some devices, the microneedles are designed so as to penetrate to a depth that does not stimulate the nerve endings and institute a pain response. Examples of microneedle devices have been described in U.S. Pat. No. 6,334,856 to Allen, et al. and U.S. Pat. No. 7,226,439 to Prausnitz, et al., both of which are incorporated herein by reference.

Unfortunately, even with the inclusion of microneedles on a transdermal device, transdermal devices are presently limited to delivery of low molecular weight agents that have a moderate lipophilicity and no charge. Even upon successful crossing of the natural dermal boundary, problems still exist with regard to maintaining the activity level of delivered agents and avoidance of foreign body and immune response.

The nanotopography of a surface adjacent to a cell has been found to affect adhesive characteristics between the two as well as to effect cell behavior including morphology, motility, cytoskeleton architecture, proliferation, and differentiation (see, e.g., Hart, et al., European Cells and Materials, Vol. 10, Suppl. 2, 2005; Lim, et al., J R Soc Interface, Mar. 22, 2005, 2(2), 97-108; Yim, et al., Biomaterials, September, 2005, 26(26), 5405-5413). As an extension of this initial research, nanotopography of supporting substrates has been examined for use in tissue engineering (see, e.g., U.S. Patent Application Publication Nos. 2008/0026464 to Borenstein, et al. and 2008/0311172 to Schapira, et al.).

What are needed in the art are improved drug delivery devices. For instance, devices that provide efficient delivery of active agents while decreasing potential immune and foreign body response to both the delivery device and the delivered agents would be beneficial.

SUMMARY

According to one embodiment, disclosed is a composite microneedle array. An array may include a microneedle assembly that includes a support having a first surface and a second surface, wherein a plurality of microneedles extend outwardly from the first surface. An array may also include a film overlaying the microneedles of the microneedle assembly that at least partially conforms to the shape of the microneedles. The film may have a first surface and a second surface. The first surface of the film may be adhered to the microneedle assembly, and the second surface of the film may include thereon a plurality of nanostructures, the nanostructures being arranged in a predetermined pattern.

Also disclosed is a method for forming a composite microneedle array. A method may include laying a film over a microneedle assembly and engaging the film with the microneedle assembly such that the film at least partially conforms to the microneedles of the array and adheres to the microneedle assembly.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIG. 12 schematically illustrates one embodiment of a microneedle including a film at a surface that defines a nanotopography that may interact with an extracellular matrix (ECM).

FIGS. 13A-13C schematically illustrate a method of draping a nanopatterned film over a microneedle of an array to form a composite microneedle array.

FIGS. 27A-27E illustrate several nanotopography patterns as described herein.

FIG. 28 is an SEM of a film including a nanopatterned surface.

FIG. 40A is a cross section of skin that was in contact with a transdermal device defining nanotopography thereon, and FIG. 40B is a cross section of skin that was in contact with a transdermal device including no pattern of nanotopography formed thereon.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

In general, a microneedle array is disclosed herein. The microneedle array is a composite structure that includes a microneedle assembly and a film applied to the surface of the assembly and contacting the microneedles. The film defines a plurality of fabricated structures on a surface. At least a portion of the structures are fabricated on a nanometer scale. As utilized herein, the term 'fabricated' generally refers to a structure that has been specifically designed, engineered, and/or constructed so as to exist at a surface and is not to be equated with a surface feature that is merely an incidental product of a formation process. Thus, there will be a predetermined pattern of nanostructures on the surface of the microneedles.

Also disclosed is a method of forming the composite arrays. A formation process may include the draping or layering of the film over the microneedle assembly such that the film at least partially conforms to the shape of the microneedles and the nano-sized structures of the film are facing away from the microneedles, i.e., the structures are exposed at the surface of the composite microneedle array. The film is engaged with the microneedle assembly and adheres to the microneedle assembly strongly enough that the film will not delaminate from the microneedle assembly during use.

The microneedle array, including a microneedle assembly and a film applied thereto that includes a plurality of nanosized structures, may be utilized in a drug delivery application. For example, a microneedle array may be configured to be placed in fluid communication with a drug delivery assembly. A drug delivery assembly may include a drug compound in fluid communication with the microneedle assembly during use. In one preferred embodiment, a microneedle assembly may be a component of a transdermal patch for drug delivery. Beneficially, the nano-sized structures located at the surface of the microneedle assembly may provide efficient delivery of active agents, including large molecular weight active agents, while decreasing immune response and foreign body response to both the drug delivery device and the agents delivered by the device.

Various aspects of the disclosure will now be described in more detail.

1. Microneedle Assembly

Figure 1:
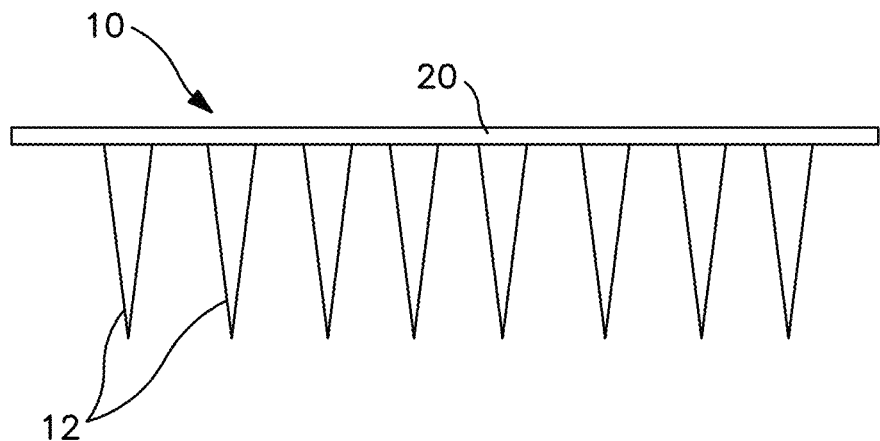
FIG. 1 schematically illustrates one embodiment of a microneedle array.

The microneedle assembly contains a plurality of microneedles that extend outwardly from a support. Referring to FIG. 1, for example, one particular embodiment of a microneedle assembly 10 is shown that contains a plurality of microneedles 12 that extend from a support 20. The support 20 may be constructed from a rigid or flexible sheet of metal, ceramic, plastic or other material. The support 20 may vary in thickness to meet the needs of the device, such as about 1000 micrometers or less, in some embodiments from about 1 to about 500 micrometers, and in some embodiments, from about 10 to about 200 micrometers.

Figure 2:
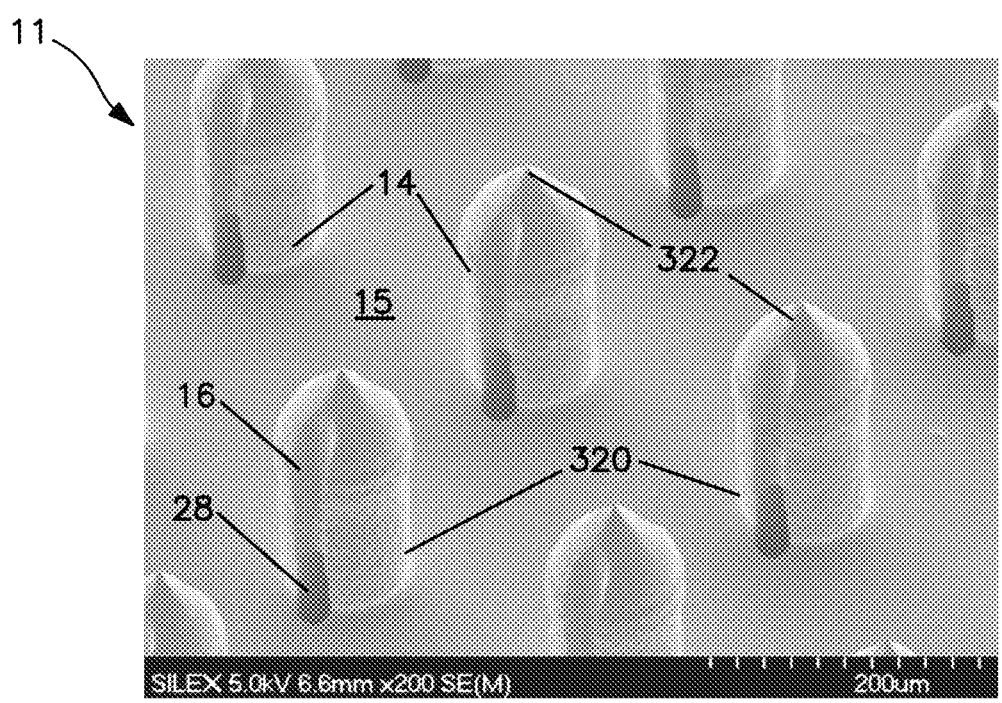
FIG. 2 is a scanning electron micrograph (SEM) image of another embodiment of a microneedle array.

FIG. 2 illustrates another embodiment of a microneedle assembly 11 each microneedle 14 in fluid communication with an aperture 28 that may be formed in the support 15. The aperture 28 extends through the support 15. The microneedles 14 extend from the surface of the support 15.

It should be understood that the number of microneedles shown in the figures is for illustrative purposes only. The actual number of microneedles used in a microneedle assembly may, for example, range from about 500 to about 10,000, in some embodiments from about 2,000 to about 8,000, and in some embodiments, from about 4,000 to about 6,000.

The size and shape of the microneedles may also vary as desired. For example, the microneedles 14 of FIG. 2 include a cylindrical portion upon which is positioned a conical portion having a tip. In alternative embodiments, however, the microneedles 14 may have an overall pyramidal shape or an overall conical shape. Regardless, the microneedle 14 typically includes a base 320 and a tip 322. As shown in FIG. 2, the base 320 is the portion of the microneedle 318 that is proximate to the surface of the support 15. The tip 322 of a microneedle 14 is the point of the microneedle that is furthest from the base 320. Although the tip 322 may be variously formed, it typically has a radius that is less than or equal to about 1 micrometer. The microneedles 14 are typically of a length sufficient to penetrate the stratum corneum and pass into the epidermis, but not penetrate through the epidermis and into the dermis in applications where it is desirable to minimize pain. In certain embodiments, the microneedles have a length (from their tip 322 to their base 320) between about 1 micrometer and about 1 millimeter in length, for instance about 500 micrometers or less, or between about 10 micrometers and about 500 micrometers, or between about 30 micrometers and abut 200 micrometers.

The size of individual needles may be optimized depending upon the desired targeting depth, the strength requirements of the needle to avoid breakage in a particular tissue type, etc. For instance, the cross-sectional dimension of a transdermal microneedle may be between about 10 nanometers (nm) and 1 millimeter (mm), or between about 1 micrometer (μm) and about 200 micrometers, or between about 10 micrometers and about 100 micrometers. The outer diameter may be between about 10 micrometers and about 100 micrometers and the inner diameter of a hollow needle may be between about 3 micrometers and about 80 micrometers. The tip typically has a radius that is less than or equal to about 1 micrometer.

The microneedles 14 may be arranged on the substrate in a variety of patterns, and such patterns may be designed for a particular use. For example, the microneedles 14 may be spaced apart in a uniform manner, such as in a rectangular or square grid or in concentric circles. The spacing may depend on numerous factors, including height and width of the microneedles 14, the characteristics of the film that will be applied to the surface of the microneedles 14, as well as the amount and type of substance that is intended to be moved through the microneedles 14. While a variety of arrangements of microneedles is useful, a particularly useful arrangement of microneedles 14 is a "tip-to-tip" spacing between microneedles of about 50 micrometers or more, in some embodiments about 100 to about 800 micrometers, and in some embodiments, from about 200 to about 600 micrometers.

The microneedles 14 may be formed of various substances such as, for example, polymers, ceramics and metals. While numerous processes may be used to manufacture microneedles, a suitable production system is MEMS (Micro-Electro-Mechanical Systems) technology and microfabrication processes. MEMS is capable of forming micromechanical and other elements such as semiconductors on a single silicon substrate using microfabrication processes such as etching, micromachining or other processes. The support 15 may be manufactured from silicon, the microneedles being subsequently formed by a microetching process. Micromolding techniques may also be used to form the microneedles 14 and support 15.

In one embodiment, the microneedles 14 may define at least one channel 16 that is in fluidic communication with at least a portion of an aperture 28 of the support 15. The dimensions of the channel 16, when present, may be specifically selected to induce capillary flow of a drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio can be determined from the average dimensions.

Figure 3:
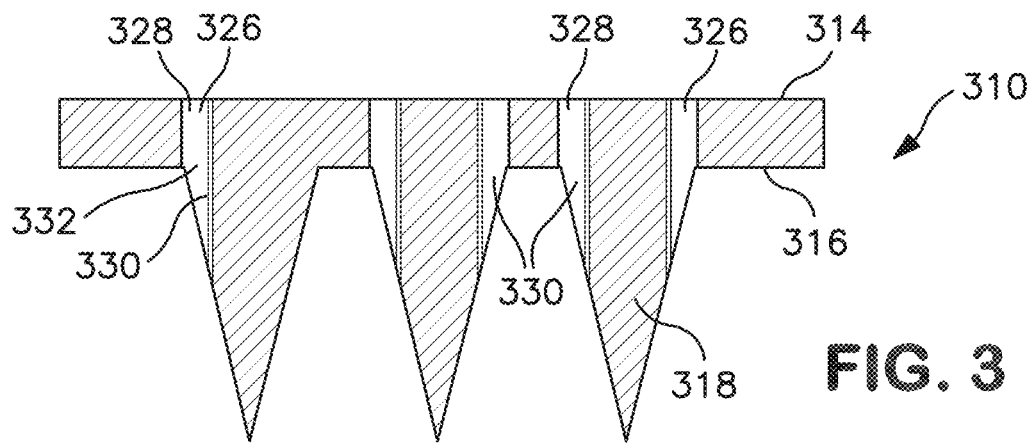
FIGS. 3 and 4 are partial cross-sectional views of microneedle arrays that may be formed in accordance with an embodiment of the present disclosure.
Figure 4:
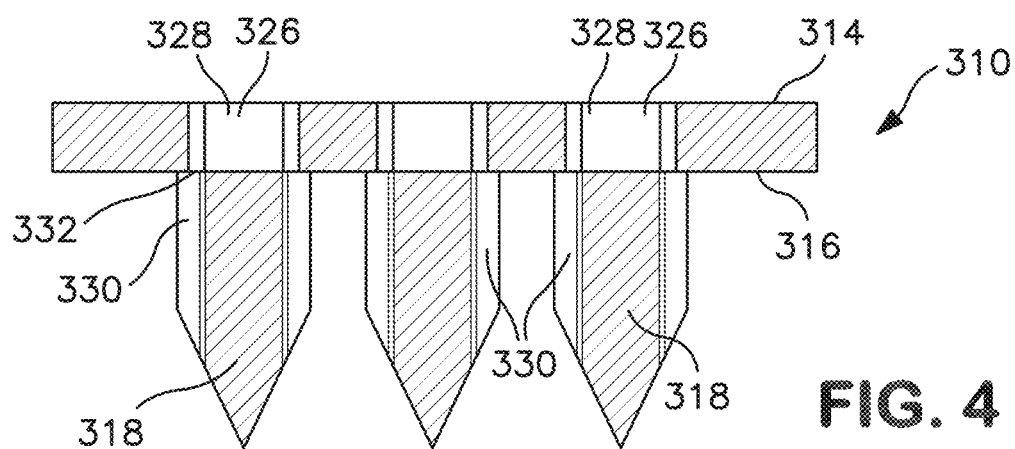

Referring to FIGS. 3-4, the illustrated microneedles 318 contain at least one channel 330. The channel may be located in a variety of different positions, such as in the interior of the microneedle, on an exterior surface, etc. In the embodiment illustrated in FIGS. 3-4, for example, the channel 330 is located on an exterior surface of the microneedle 318. The cross-section of a channel may be any suitable shape. For example the channel 16 shown in FIG. 2 is substantially U-shaped. The channel may be arcuate or have any other configuration suitable for moving a substance therethrough, such as, for example, V-shaped or C-shaped. Regardless, and referring again to FIGS. 3-4, a pathway 326 may be formed by the channel 330 and the aperture 328, which meet at a junction 332 that is generally located in the plane of the surface 316. Each microneedle 318 may deliver or extract drug compounds through the skin via the pathway 326, as depicted in FIGS. 3-4. The pathway 326 enables the compound to flow from the first surface 314 through the aperture 328, the junction 332 and exit into the channel 330. By enabling the compound to flow through the support and directly into the channel 330, more precise control over the delivery location and the amount of substance delivered may be provided.

In certain embodiments and as shown in FIG. 3, an aperture 328 is aligned with a single channel 330 via a junction 332. Alternately and as shown in FIG. 4, a single aperture 328 may feed two or more separate channels 330.

The channel 330 may extend from the junction 332 at the base 320 of the microneedle to the tip 322. In other embodiments, the channel 330 may not extend the full length of the microneedle 318 to the tip 322, as shown in FIGS. 3-4. Each microneedle 318 may include more than one channel 330, as in the embodiment of FIG. 4. Alternate embodiments may include more channels if desired. The channel 330 may be variously positioned on the exterior surface 324, forming a substantially linear path from the base 320 towards the tip 322, or forming a winding or circuitous path along the exterior surface 324. In microneedles where two or more channels are present, the channels 330 may be variously spaced around the microneedle 318 in a symmetrical or asymmetrical manner.

II. Nanopatterned Film

Figure 5A:
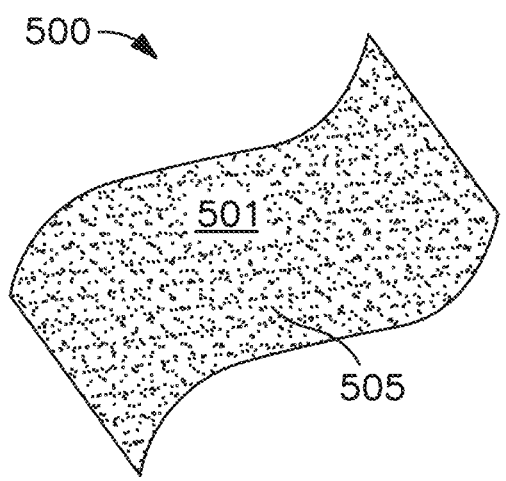
FIGS. 5A and 5B illustrate opposite sides of a nanopatterned film as may be applied to a microneedle array.
Figure 5B:
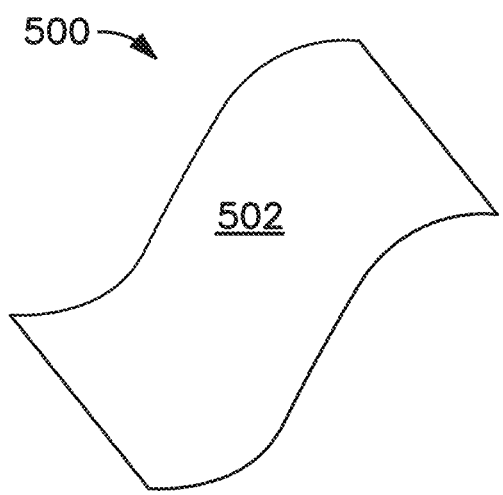

The microneedle assembly may be draped or layered with a film that defines a plurality of structures on a surface. FIGS. 5A and 5B schematically illustrate the patterned (FIG. 5A) and unpatterned (FIG. 5B) sides of one embodiment of a film 500 defining a first side 501 and a second side 502. A plurality of structures 505 is formed on the first side 501 of film 500. Film 500 may have a thickness from the first side 501 to the second side 502 of greater than about 2 micrometers, in one embodiment. For instance film 500 may have a thickness between about 1 micrometer and about 1 millimeter. A film 500 may have a thickness between about 5 micrometers and about 200 micrometers, or between about 5 micrometers and about 100 micrometers, in one embodiment.

A film 500 may include a plurality of identical structures formed on the first surface 501 or may include structures formed of various sizes, shapes and combinations thereof in a random or nonrandom pattern. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles.

A complex nanotopography may be formed on a film that may define a fractal or fractal-like geometry. As utilized herein, the term "fractal" generally refers to a geometric or physical structure or pattern having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure or pattern having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For instance, it may be regular and relatively easily described in traditional Euclidean geometric language, whereas a fractal may not.

A film 500 may include structures of the same general shape (e.g., pillars) and the pillars may be formed to different scales of measurement (e.g., nano-scale pillars as well as micro-scale pillars). Alternatively, a film may include at a surface structures that vary in both scale size and shape or that vary only in shape while formed to the same nano-sized scale. Structures may vary with regard to size and/or shape and may form a complex nanotopography.

At least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension may generally be greater than about 5 nanometers, for instance greater than about 10 nanometers, or greater than about 20 nanometers. For example, the nanostructures may define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

FIG. 4 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes may include larger structures having a cross-sectional dimension formed on a larger scale, e.g., microstructures having a cross-sectional dimension greater than about 500 nanometers in combination with smaller nanostructures. In one embodiment, microstructures of a complex nanotopography may have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 8 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 6 have a cross-sectional dimension of about 400 nanometers, and pillars 104 have a cross-sectional dimension of about 200 nanometers.

Figure 6:
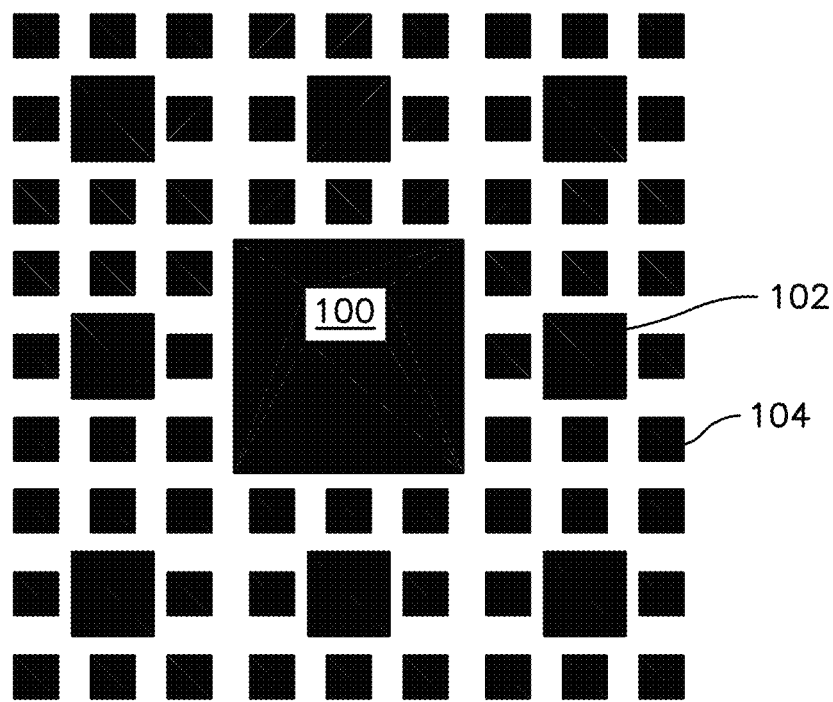
FIG. 6 illustrates one embodiment of a complex pattern that may be formed on a film surface.

A nanotopography may be formed of any number of different elements. For instance, a pattern of elements may include two different elements, three different elements, an example of which is illustrated in FIG. 6, four different elements, or more. The relative proportions of the recurrence of each different element may also vary. In one embodiment, the smallest elements of a pattern will be present in larger numbers than the larger elements. For instance in the pattern of FIG. 6, there are eight pillars 104 for each pillar 102, and there are eight pillars 102 for the central large pillar 100. As elements increase in size, there may generally be fewer recurrences of the element in the nanotopography. By way of example, a first element that is about 0.5, for instance between about 0.3 and about 0.7 in cross-sectional dimension as a second, larger element may be present in the topography about five times or more than the second element. A first element that is approximately 0.25, or between about 0.15 and about 0.3 in cross-sectional dimension as a second, larger element may be present in the topography about 10 times or more than the second element.

The spacing of individual elements may also vary. For instance, center-to-center spacing of individual structures may be between about 50 nanometers and about 1 micrometer, for instance between about 100 nanometers and about 500 nanometers. For example, center-to-center spacing between structures may be on a nano-sized scale. For instance, when considering the spacing of nano-sized structures, the center-to-center spacing of the structures may be less than about 500 nanometers. This is not a requirement of a topography, however, and individual structures may be farther apart. The center-to-center spacing of structures may vary depending upon the size of the structures. For example, the ratio of the average of the cross-sectional dimensions of two adjacent structures to the center-to-center spacing between those two structures may be between about 1:1 (e.g., touching) and about 1:4, between about 1:1.5 and about 1:3.5, or between about 1:2 and about 1:3. For instance, the center to center spacing may be approximately double the average of the cross-sectional dimensions of two adjacent structures. In one embodiment, two adjacent structures each having a cross-sectional dimension of about 200 nanometers may have a center-to-center spacing of about 400 nanometers. Thus, the ratio of the average of the diameters to the center-to-center spacing in this case is 1:2.

Structure spacing may be the same, i.e., equidistant, or may vary for structures in a pattern. For instance, the smallest structures of a pattern may be spaced apart by a first distance, and the spacing between these smallest structures and a larger structure of the pattern or between two larger structures of the pattern may be the same or different as this first distance.

For example, in the pattern of FIG. 6, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures may be equidistant from one another or any variation in distances. In one embodiment, different structures may be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, nanostructures may have an aspect ratio falling within any of these ranges.

Figure 7:
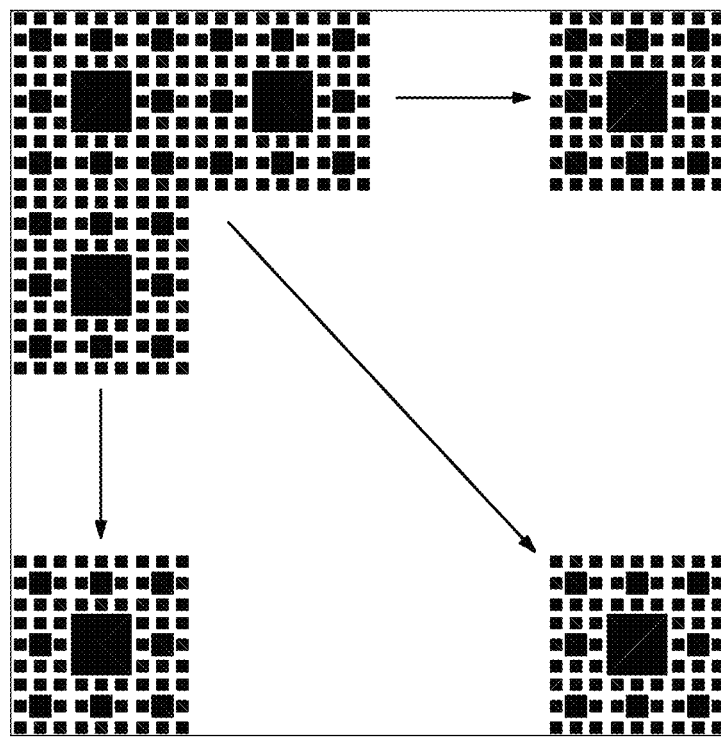
FIG. 7 illustrates a pattern including multiple iterations of the complex pattern of FIG. 6.

A film surface may include a single instance of a pattern, as shown in FIG. 6, or may include multiple iterations of the same or different patterns. For example, FIG. 7 illustrates a surface pattern including the pattern of FIG. 6 in multiple iterations over a surface.

Figures 8A, 8B:
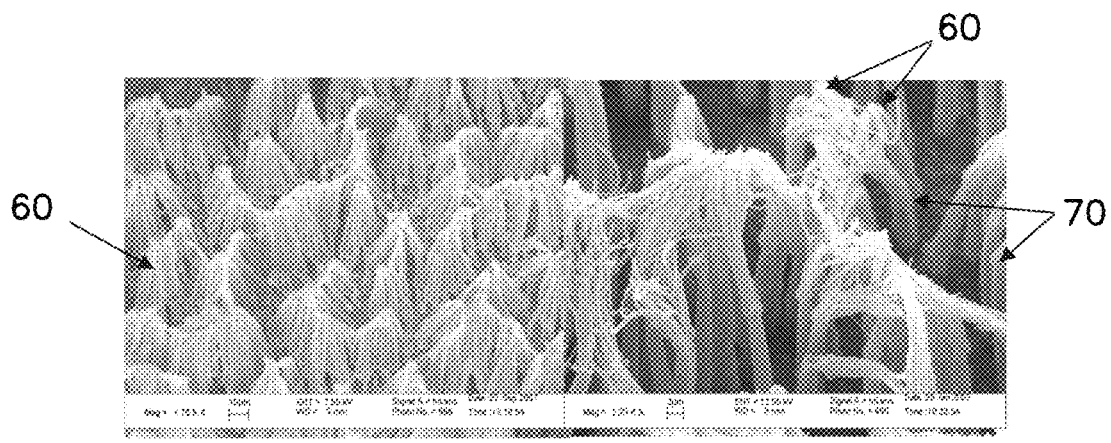
FIGS. 8A-8D illustrate examples of complex fractal and fractal-like nanotopographies.

FIGS. 8A and 8B illustrate increasing magnification images of another example of a complex nanotopography. The nanotopography of FIGS. 8A and 8B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 8A and 8B). Structures formed on a surface that have an aspect ratio greater than about 1 may be flexible, as are the structures illustrated in FIGS. 8A and 8B, or may be stiff.

Figures 8C, 8D:
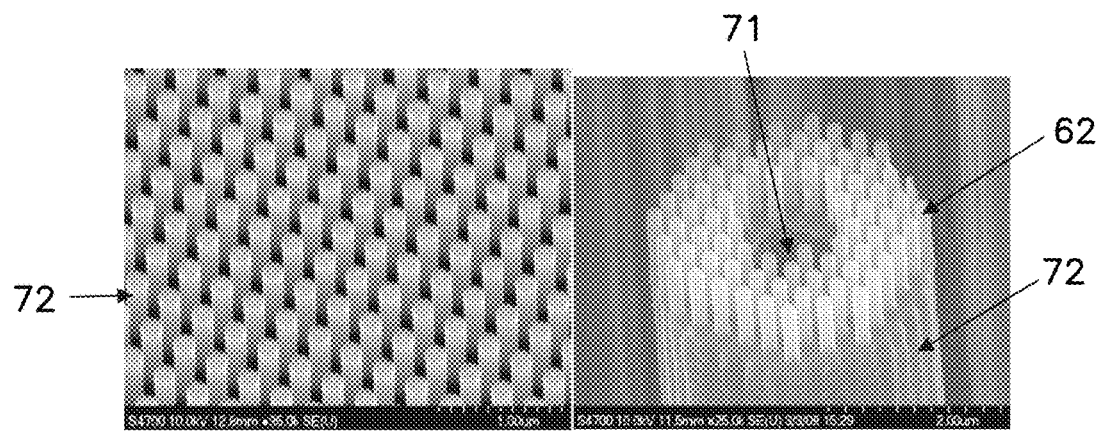

FIGS. 8C and 8D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 8C and 8D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 9:
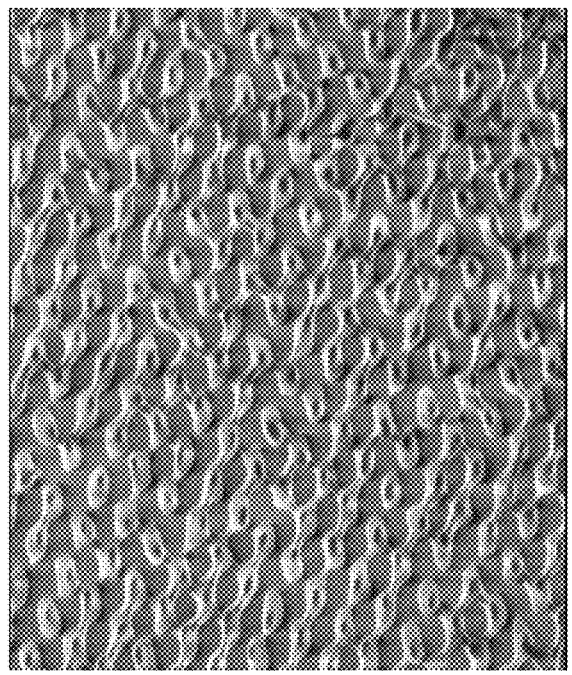
FIG. 9 illustrates another complex pattern that may be formed on a film surface.

FIG. 9 illustrates another pattern including nano-sized structures as may be formed on the surface of the film. As may be seen, in this embodiment, individual pattern structures may be formed at the same general size, but with different orientations and shapes from one another.

Figure 10A:
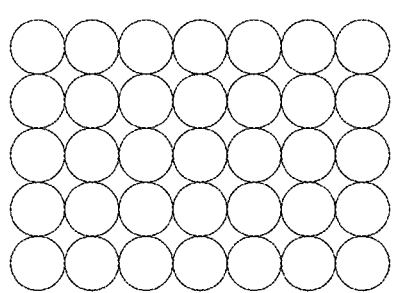
FIGS. 10A-10C illustrates exemplary packing densities as may be utilized for nano-sized structures as described herein including a square packing design (FIG. 10A), a hexagonal packing design (FIG. 10B), and a circle packing design (FIG. 10C).
Figure 10B:
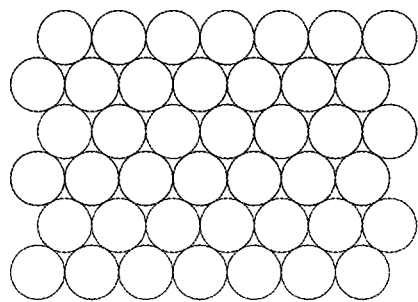
Figure 10C:
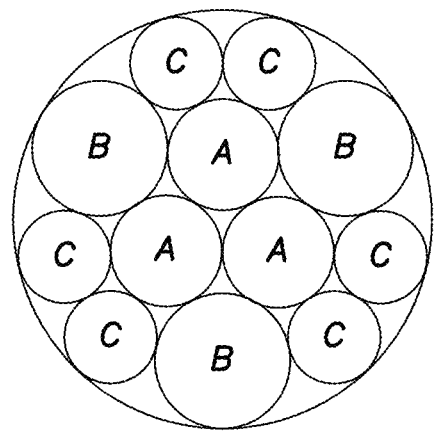

The pattern of the individual structures may be designed so as to affect the packing density. For instance, square packing (FIG. 10A), hexagonal packing (FIG. 10B), or some variation thereof may be utilized to pattern the structures on a film. When designing a pattern in which various sized structures of cross sectional areas A, B, and C are adjacent to one another on a substrate, circle packing as indicated in FIG. 10C may be utilized. Of course, variations in packing density and determination of associated alterations in characteristics of a surface are well within the abilities of one of skill in the art.

The formation of nanotopography on a film surface may increase the surface area of the film without a corresponding increase in volume. In general, the surface area to volume ratio of the film may be greater than about 10,000 cm$^{-1}$, greater than about 150,000 cm$^{-1}$, or greater than about 750,000 cm$^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319), incorporated herein by reference. The BET surface area may be less than about 5 m$^2$/g, in one embodiment, for instance between about 0.1 m$^2$/g and about 4.5 m$^2$/g, or between about 0.5 m$^2$/g and about 3.5 m$^2$/g. Values for surface area and volume may also be estimated from the geometry of molds used to form a surface, according to standard geometric calculations. For example, the volume may be estimated according to the calculated volume for each pattern element and the total number of pattern elements in a given area, e.g., over the surface of a single microneedle.

The nanotopography of a film may be characterized through determination of the fractal dimension of the pattern of structures on the film. In one embodiment, nanotopography of a surface of the device may exhibit a fractal dimension of greater than about 1, for instance between about 1.2 and about 5, between about 1.5 and about 3, or between about 1.5 and about 2.5.

The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

Figure 11:
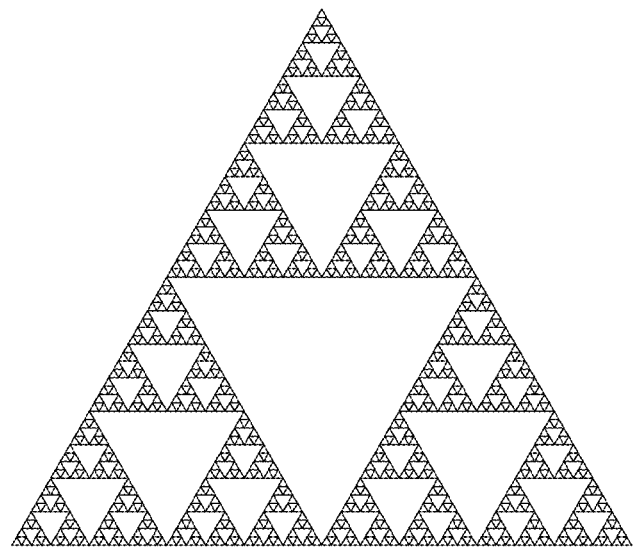
FIG. 11 illustrates the fractal pattern known as the Sierpenski triangle.

For example, when considering the two dimensional fractal known as the Sierpenski triangle illustrated in FIG. 11, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 6 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

A film surface may be characterized by measurement of surface roughness. Methods for determining surface roughness are generally known in the art. For instance, an atomic force microscope process in contact or non-contact mode may be utilized according to standard practice to determine the surface roughness of a material. Surface roughness that may be utilized to characterize a microneedle may include the average surface roughness ($R_A$), the root mean square roughness, the skewness, and/or the kurtosis. In general, the average surface roughness (i.e., the arithmetical mean height of the surface are roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The film may be characterized by the elastic modulus of the nanopatterned surface, for instance by the change in elastic modulus upon the addition of a nanotopography to a surface. In general, the addition of a plurality of structures forming nanotopography on a surface may decrease the elastic modulus of a material, as the addition of nano-sized structures on a surface will lead to a reduction in continuity of the surface and a related change in surface area. As compared to a similar surface formed according to the same process and of the same materials, but for a pattern of nanotopography on the surface, the film including nanotopography thereon may exhibit a decrease in elastic modulus of between about 35% and about 99%, for instance between about 50% and about 99%, or between about 75% and about 80%. By way of example, the effective compression modulus of a nanopatterned surface may be less than about 50 MPa, or less than about 20 MPa. In one embodiment the effective compression modulus may be between about 0.2 MPa and about 50 MPa, between about 5 MPa and about 35 MPa, or between about 10 MPa and about 20 MPa. The effective shear modulus may be less than about 320 MPa, or less than about 220 MPa. For instance, the effective shear modulus may be between about 4 MPa and about 320 MPa, or between about 50 MPa and about 250 MPa, in one embodiment.

The film including nanotopography thereon may also exhibit an increase in surface energy as compared to a similar film that does not have a surface defining a pattern of nanotopography thereon. For instance, a film including a nanotopography formed thereon may exhibit an increase in surface energy as compared to a similar film of the same materials and formed according to the same methods, but for the inclusion of a pattern of nanotopography on a surface. For instance, the water contact angle of a surface including a nanotopography thereon may be greater than about 80°, greater than about 90°, greater than about 100°, or greater than about 110°. For example, the water contact angle of a surface may be between about 80° and about 150°, between about 90° and about 130°, or between about 100° and about 120°, in one embodiment.

The film including a plurality of nanostructures thereon may be formed according to any known method. A nanostructured film may be formed in a single or multi-step process. For instance, a film may first be formed, and then a pattern of nanostructures may be molded or built onto a surface of the film. In another embodiment, a single step process in which the film is formed with the structures thereon may be carried out.

In one embodiment, a master defining a plurality of nanostructures thereon may be formed and then a film may be molded through press molding against the master. The pattern of structures may be formed on a master according to any nanofabrication method including, without limitation, nanoimprinting, lithography, embossing molding, and so forth.

Lithography techniques, including photolithography, e-beam lithography, X-ray lithography, and so forth may be utilized for primary pattern definition and formation of a master. Self-assembly technologies including phase-separated block copolymer, polymer demixing and colloidal lithography techniques may also be utilized in forming the nanotopography on the surface of the master.

Combinations of methods may be used, as is known. For instance, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer de-mixing techniques.

Structure diameter, shape, and pitch may be controlled via selection of appropriate materials and methods. For example, etching of metals initially evaporated onto colloidal-patterned substrates followed by colloidal lift-off generally results in prism-shaped pillars. An etching process may then be utilized to complete the structures as desired. Ordered non-spherical polymeric nanostructures may also be fabricated via temperature-controlled sintering techniques, which form a variety of ordered trigonal nanometric features in colloidal interstices following selective dissolution of polymeric nanoparticles. These and other suitable formation processes are generally known in the art (see, e.g., Wood, J R Soc Interface, 2007 Feb. 22; 4(12): 1-17, incorporated herein by reference).

Other methods as may be utilized in forming a master include utilization of ultra-high precision laser machining techniques, examples of which have been described by Hunt, et al. (U.S. Pat. No. 6,995,336) and Guo, et al. (U.S. Pat. No. 7,374,864), both of which are incorporated herein by reference.

Structures may also be formed according to chemical addition processes. For instance, film deposition, sputtering, chemical vapor deposition (CVD), epitaxy (vapor phase, liquid phase, and molecular beam), electroplating, and so forth may be utilized for building nanostructures on a master.

Self-assembled monolayer (SAM) processes as are known in the art may be utilized to form a pattern of nanostructures. For instance, the ability of block copolymers to self-organize may be used to form a monolayer pattern on a surface. The pattern may then be used as a template for the growth of desired structures, e.g., colloids, according to the pattern of the monolayer.

By way of example, a two-dimensional, cross-linked polymer network may be produced from monomers with two or more reactive sites. Such cross-linked monolayers have been made using SAM (e.g., a gold/alkyl thiol system) or Langmuir-Blodgett (LB) monolayer techniques (Ahmed et al., Thin Solid Films 187: 141-153 (1990)) as are known in the art. The monolayer may be crosslinked, which may lead to formation of a more structurally robust monolayer.

The monomers used to form a patterned monolayer may incorporate all the structural moieties necessary to affect the desired polymerization technique and/or monolayer formation technique, as well as to influence such properties as overall solubility, dissociation methods, and lithographic methods. A monomer may contain at least one and more often at least two, reactive functional groups.

A molecule used to form an organic monolayer may include any of various organic functional groups interspersed with chains of methylene groups. For instance a molecule may be a long chain carbon structure containing methylene chains to facilitate packing. The packing between methylene groups may allow weak Van der Waals bonding to occur, enhancing the stability of the monolayer produced and counteracting the entropic penalties associated with forming an ordered phase. In addition, different terminal moieties such as hydrogen-bonding moieties may be present at one terminus of the molecules, in order to allow growth of structures on the formed monolayer, in which case the polymerizable chemical moieties may be placed in the middle of the chain or at the opposite terminus. Any suitable molecular recognition chemistry may be used in forming the assembly. For instance, structures may be assembled on a monolayer based on electrostatic interaction, Van der Waals interaction, metal chelation, coordination bonding (i.e., Lewis acid/base interactions), ionic bonding, covalent bonding, or hydrogen bonding.

When utilizing a SAM-based system, an additional molecule may be utilized to form the template. This additional molecule may have appropriate functionality at one of its termini in order to form a SAM. For example, on a gold surface, a terminal thiol may be included. There are a wide variety of organic molecules that may be employed to effect replication. Topochemically polymerizable moieties, such as dienes and diacetylenes, are particularly desirable as the polymerizing components. These may be interspersed with variable lengths of methylene linkers.

For an LB monolayer, only one monomer molecule is needed because the molecular recognition moiety may also serve as the polar functional group for LB formation purposes. Lithography may be carried out on a LB monolayer transferred to a substrate, or directly in the trough. For example, an LB monolayer of diacetylene monomers may be patterned by UV exposure through a mask or by electron beam patterning.

Monolayer formation may be facilitated by utilizing molecules that undergo a topochemical polymerization in the monolayer phase. By exposing the assembling film to a polymerization catalyst, the film may be grown in situ, and changed from a dynamic molecular assembly to a more robust polymerized assembly for use as the master.

Techniques useful in patterning a monolayer include, but are not limited to, photolithography, e-beam techniques, focused ion-beam techniques, and soft lithography. Various protection schemes such as photoresist may be used for a SAM-based system. Likewise, block copolymer patterns may be formed on gold and selectively etched to form patterns. For a two-component system, patterning may also be achieved with readily available techniques.

Soft lithography techniques may be utilized to pattern the monolayer in which ultraviolet light and a mask may be used for patterning. For instance, an unpatterned base monolayer may be used as a platform for assembly of a UV/particle beam reactive monomer monolayer. The monomer monolayer may then be patterned by UV photolithography, e-beam lithography, or ion beam lithography, even though the base SAM is not patterned.

Growth of structures on a patterned monolayer may be achieved by various growth mechanisms, such as through appropriate reduction chemistry of a metal salts and the use of seed or template-mediated nucleation. Using the recognition elements on the monolayer, inorganic growth may be catalyzed at this interface by a variety of methods. For instance inorganic compounds in the form of colloids bearing the shape of the patterned organic monolayer may be formed. For instance calcium carbonate or silica structures may be templated by various carbonyl functionalities such as carboxylic acids and amides. By controlling the crystal growth conditions, it is possible to control the thickness and crystal morphology of the mineral growth. Titanium dioxide may also be templated.

Templated electroless plating techniques may be used to synthesize metals using existing organic functional groups. In particular, by chelating metal atoms to the carbonyl moieties of the organic pattern, electroless metal deposition may be catalyzed on the pattern, forming patterned metallic colloids. For instance, Cu, Au, Ni, Ag, Pd, Pt and many other metals plateable by electroless plating conditions may be used to form metal structures in the shape of the organic monolayer. By controlling the electroless plating conditions, it is possible to control the thickness of the plated metal structures.

Other 'bottom-up' type growth methods as are known in the art may be utilized for forming the master, for example a method as described in U.S. Pat. No. 7,189,435 Tuominen, et al., which is incorporated herein by reference, may be utilized. According to this method, a conducting or semi-conducting substrate (for example, a metal, such as gold) may be coated with a block copolymer film (for example, a block copolymer of methylmethacrylate and styrene), where one component of the copolymer forms nanoscopic cylinders in a matrix of another component of the copolymer. A conducting layer may then be placed on top of the copolymer to form a composite structure. Upon vertically orientation of the composite structure, some of the first component may be removed, for instance by exposure to UV radiation, an electron beam, or ozone, degradation, or the like to form nanoscopic pores in that region of the second component.

In another embodiment, described in U.S. Pat. No. 6,926,953 to Nealey, et al., incorporated herein by reference, copolymer structures may be formed by exposing a substrate with an imaging layer thereon, for instance an alkylsiloxane or an octadecyltrichlorosilane self assembled monolayer, to two or more beams of selected wavelengths to form interference patterns at the imaging layer to change the wettability of the imaging layer in accordance with the interference patterns. A layer of a selected block copolymer, for instance a copolymer of polystyrene and poly(methyl methacrylate) may then be deposited onto the exposed imaging layer and annealed to separate the components of the copolymer in accordance with the pattern of wettability and to replicate the pattern of the imaging layer in the copolymer layer. Stripes or isolated regions of the separated components may thus be formed with periodic dimensions in the range of 100 nanometers or less.

A master may be utilized to form the desired structures on a flexible film. The master may be a positive master or a negative master, depending upon the molding method used to form the film from the master. For instance, the master may be a negative mold master, defining the negatives of the nanostructures to be formed on a film, and the film may be formed or molded against the negative master through application of heat and/or pressure. In another embodiment, a positive master may be used to form a negative master, for instance via an electroforming process, and the negative master may then be used in a film forming process. A process of electroforming involves placing the positive mold master into an electroforming tank that deposits a metal around the features of the master. This may be any suitable metal. The metal is deposited to a desired thickness at which point the positive mold master is separated from the electroformed metal creating the negative mold components. This form of a mold is typically called an electroform. Following formation, an electroform may then be cut utilized to mold a film surface.

In one embodiment, a pattern from a master may be transferred to a film according to a process and device as described in U.S. Pat. No. 7,754,131 to Olsson, et al., which is incorporated herein by reference. For instance, the master may be located in conjunction with an aligned, nonpatterned film. The master may then be pressed against the film under sufficient heat and pressure so as to transfer the pattern to the film. Preferred pressures and temperatures may depend upon the material that forms the film. For example, the film may be heated to a temperature up to about 500° C. prior to being pressed against the master. Other methods and devices for forming a pattern of nanostructures on a film as are known in the art may alternatively be utilized such as those described in U.S. Pat. Nos. 6,923,930, 7,022,465, 7,041,228, 7,137,336, 7,195,734, 7,252,492, 7,670,127, 7,670,452, 7,687,007, 7,704,425, 7,717,693, 7,855,046, and 7,862,849, all of which are incorporated herein by reference.

The film may generally be a biocompatible polymeric film formed of a moldable thermoplastic or thermoset polymer. By way of example, a film may include homopolymers and/or copolymers of a polyolefin (e.g., polypropylene, polyethylene), a polystyrene, a polycarbonate, a polymethacrylate (e.g., polymethylmethacrylate), and so forth. In one embodiment, a film may include biodegradable polymers as are known in the art including, without limitation, homopolymers and copolymers of polylactides (e.g., PLA-co-PGA copolymers), polyhydroxyalkanoates, and the like.

III. Formation of Composite Array

The film formed with a plurality of nanosized structures on at least one side may be applied to the microneedle assembly to form the composite microneedle array. FIG. 12 schematically illustrates the ends of two representative microneedles 22 that include a film 26 defining a fabricated nanostructure on the surface of the microneedles 22. In this particular embodiment, microneedles 22 define a central bore 24 as may be used for delivery of an agent via the microneedles 22. The surface 25 of microneedle 22 has been layered with a film 26 that defines a pattern of nanostructures thereon. In this particular embodiment, the nanotopography of film 26 defines a random pattern on the surface.

FIGS. 13A-13C schematically illustrate a formation process for a composite microneedle array. Microneedle assembly 418 includes a microneedle 414 formed on a surface. In FIG. 13A, both a side view and a top view of microneedle 414 may be seen. Microneedle 414 includes channels 412 and apertures 410 aligned with channels 412. FIG. 13B illustrates a film 420 includes a plurality of nanostructures 424 formed on a first side of the film 420. As shown in FIG. 13C, a composite microneedle array 430 includes the film 420 applied to the surface of the microneedle 414.

The film 420 is draped over and engaged with the microneedle 414 so that it conforms to at least a portion of the shape of the microneedle. This may be accomplished in one embodiment through application of pressure to the film 420, optionally in conjunction with heat to conform the film to the shape of the microneedle as well as to adhere the film to the microneedle surface. For example, the draped microneedle may be held on a heated vacuum box (e.g., about 3 inches H$_2$O vacuum) at an elevated temperature that is below the softening point of the polymeric material that forms the film 420 (e.g., between about 100° C. and about 130° C.) for a period of time (e.g., between about 15 minutes and about one hour) to at least partially conform the film to the surface of the microneedles while maintaining the nanopatterned surface of the film. Thus, in this application, the film 420 is pulled down to engage with the surface of the microneedle 414. The preferred pressure and temperature for any specific system may depend upon the specific materials involved, e.g., the polymeric material of the film, as well as the size and materials of the microneedles of the microneedle assembly.

In another embodiment, a film 420 may be engaged with the surface of the microneedle 414 through application of pressure to the top of the film 420, optionally with the application of heat. For example, the film 420 may be draped over the surface of a microneedle assembly and force may be applied to the film surface to push the film 420 against the assembly and so engage and at least partially conform the film 420 to the surface of the microneedles of the assembly. In one embodiment, a negative of the surface of the microneedle assembly may be pressed against the film 420 so as to engage the film 420 with the microneedle assembly 418. In one embodiment, a pressing device may contact the film at certain locations of the film, for instance where the film 420 meets the surface 440 of the microneedle assembly that is between individual microneedles, and/or where the film 420 overlays the channels 412, and may avoid contact with the film 420 where the film 420 overlays the microneedles 414, so as to avoid damage to the nanostructures 424 through excess force being placed upon the nanostructures 424 during the engagement process.

In one embodiment, a pressing device may apply direct pressure to the film 420 at those locations where the film 420 overlays the channels 412. This may serve to engage the film 420 with the microneedle assembly 418 and may also form a perforation in the film 420 at the channels 412, which may aid flow of an agent through the composite microneedle device.

In the embodiment of FIG. 13, the film 420 is continuous over the tip 422 of the microneedle 414. During use, pressure may be applied to the device, for instance in applying a transdermal patch to the skin surface of a user, and during application a perforation may form in the film 420 at or near the microneedle tip 422. According to another embodiment, pressure may be applied to the microneedle tip 422 prior to use, for instance during engagement of the film 420 with the microneedle array 418, or during formation of a drug delivery device that incorporates the composite microneedle array 430, and this may form a perforation in the film 420 that is layered over the microneedle assembly 418. A perforation in the film 420 at the microneedle tip 422 and/or at the channels 412 provides a route for an agent to be delivered from the drug delivery device to a delivery site. According to another embodiment, the film may be formed so as to be porous to the agent(s) to be delivered by the composite array, and the agents may diffuse across the film via the porosity, for instance upon exit from channels of the microneedles.

The surface of a composite microneedle array may be functionalized for improved interaction with tissues or individual cells during use. For instance, one or more biomolecules such as polynucleotides, polypeptides, entire proteins, polysaccharides, and the like may be bound to a structured surface prior to use. In some embodiments, a surface including nanosized structures thereon may already contain suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality. The functionalization of the film surface may be carried out prior to formation of the structures on the surface. Additionally, the functionalization of the film surface may take place prior to applying the film to the surface of the microneedle assembly or following the application process, as desired.

Materials as may be desirably bound to the surface of a composite microneedle array may include ECM proteins such as laminins, tropoelastin and/or elastin, tropocollagen and/or collagen, fibronectin, and the like. Short polypeptide fragments may be bound to the surface of a patterned device such as an RGD sequence, which is part of the recognition sequence of integrin binding to many ECM proteins. Thus, functionalization of a nanostructured surface with RGD may encourage interaction of the device with ECM proteins and further limit foreign body response to the device during use.

IV. Representative Methods of Use

The composite microneedle array may be used for interaction with tissue, such as in delivery of a bioactive agent to a cell. For example, the microneedle array may be a component of a transdermal patch used to deliver an agent to the tissue or to one or more cell types of the tissue, or may be used for structural support of a tissue, for removal of a portion or component of the tissue, and so forth. The microneedle array may be used in one embodiment for transport of a substance across one or more layers of the skin.

During use, the nanotopography of the array may interact with surrounding biological components and regulate or modulate (i.e., change) intracellular and/or intercellular signal transduction associated with cell/cell interactions, endocytosis, inflammatory response, and so forth. For instance, through interaction between the nanotopography on a surface of the microneedles and surrounding biological materials or structures, the device may regulate and/or modulate membrane potential, membrane proteins, and/or intercellular junctions (e.g., tight junctions, gap junctions, and/or desmasomes). The microneedle array may be utilized for transdermal delivery of agents or withdrawal of materials across biological barriers such as the skin, the blood-brain barrier, mucosal tissues, blood and lymph vessels, and so forth without instigating a foreign body or immune response.

Structures of the nanotopography may mimic and/or interact with one or more ECM protein such as collagen, laminin, fibronectin, etc. Cells in the local area surrounding the microneedles may maintain an anti-inflammatory microenvironment as the microneedle surfaces may better mimic the local environment either directly or indirectly, e.g., due to protein adsorption at the surface. Thus, materials may be delivered by use of the device without development of a foreign body or immune response.

In one embodiment, the nanotopography of an array may interact with one or more components of the contacting epithelial tissue to increase porosity of the tissue via paracellular and/or transcellular transport mechanisms. Epithelial tissue as may be rendered more porous by use of a composite microneedle array may include both simple and stratified epithelium, including both keratinized epithelium and transitional epithelium. Epithelial tissue encompassed herein may include any cell types of an epithelial layer including, without limitation, keratinocytes, squamous cells, columnar cells, cuboidal cells and pseudostratified cells.

Interaction of the nanotopography of a device with components of a cell network or layer of the epidermis may modulate (i.e., change) the structure of intercellular junctions therein. An intracellular junction may be at least one junction selected from the group consisting of tight junctions, gap junctions, and desmasomes. By way of example, interaction between biological components and structures of the nanotopography may modulate proteins of a cellular network so as to induce the opening of tight junctions of the stratum *granulosum*, thereby providing improved delivery of an active agent across the epidermis, and in one particular embodiment, a high molecular weight active agent. Tight junctions have been found in the stratum *granulosum* and opening of the tight junctions may provide a paracellular route for improved delivery of active agents, particularly large molecular weight active agents and/or agents that exhibit low lipophilicity that have previously been blocked from transdermal delivery.

Due to improved interaction with surrounding biological components, the devices may facilitate improved uptake of a delivered agent. For example, the pharmacokinetic (PK) profile (i.e., the profile of absorption through the epithelial membranes) of a protein therapeutic may be enhanced through utilization of a device including a pattern of nanotopography. By way of example, a protein therapeutic having a molecular weight of over 100 kDa, for instance between about 100 kDa and about 200 kDa, or about 150 kDa, may be delivered transdermally via a patch including a composite microneedle array. In one embodiment, a patch may be utilized to deliver a single dose of the protein therapeutic, for instance between about 200 and about 500 μL, or about 250 μL. Following attachment of the transdermal patch to the skin, the recipient may exhibit a PK profile that reflects a rapid rise in blood serum concentration up to between about 500 and about 1000 nanograms therapeutic per milliliter per square centimeter of patch area, for instance between about 750 and about 850 nanograms therapeutic per milliliter per square centimeter patch area, within about 1 to about 4 hours of administration. This initial rapid rise in blood serum level, which reflects rapid uptake of the therapeutic across the dermal barrier, may be followed by a less rapid decline of blood serum concentration over between about 20 and about 30 hours, for instance over about 24 hours, down to a negligible blood serum concentration of the therapeutic. Moreover, the rapid uptake of the delivered therapeutic may be accompanied by little or no inflammation. Specifically, in addition to promoting improved delivery of an agent across a transdermal barrier, the devices may also limit foreign body response and other undesirable reactions, such as inflammation. Use of previously known devices, such as transdermal patches with no nanotopography defined at the skin contacting surface, often led to local areas of inflammation and irritation.

V. Devices

Devices may be associated with an agent for delivery via the microneedle array. For instance, a transdermal microneedle patch may be utilized for delivery of materials beneath the stratum corneum to the stratum *spinosum* or the stratum germinativum, or even deeper into the dermis. In general, an agent may be transported across the stratum corneum in conjunction with the microneedle, e.g., within the microneedle, at the surface of the microneedle, or at the film surface that covers the microneedle.

The device may include a reservoir, e.g., a vessel, a porous matrix, etc., that may store an agent and provide the agent for delivery. The device may include a reservoir within the device itself. For instance, the device may include a hollow, or multiple pores that may carry one or more agents for delivery. The agent may be released from the device via degradation of a portion or the entire device or via diffusion of the agent from the device.

Figure 14A:
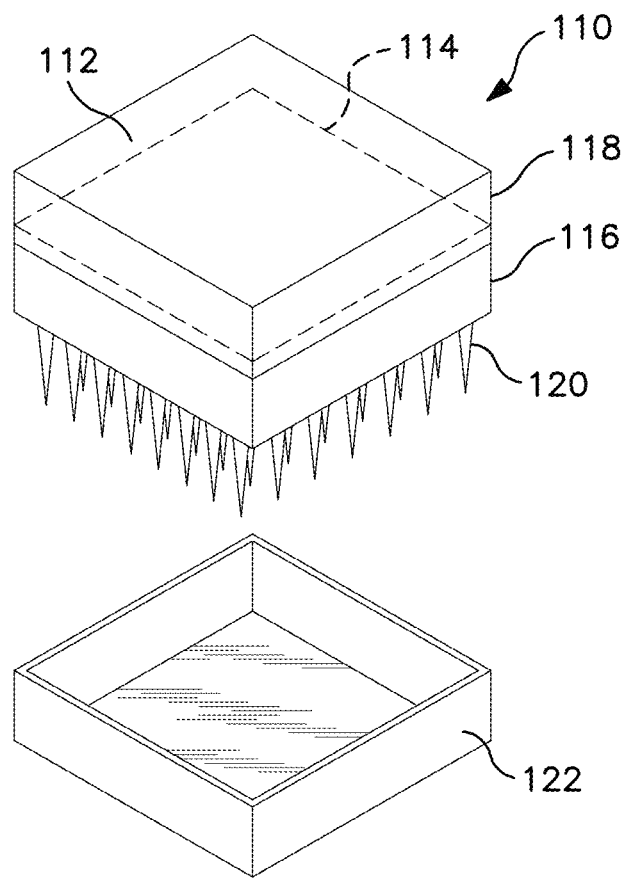
FIGS. 14A and 14B schematically illustrate one embodiment of a drug delivery device in an exploded view (FIG. 14A) and assembled (FIG. 14B).
Figure 14B:
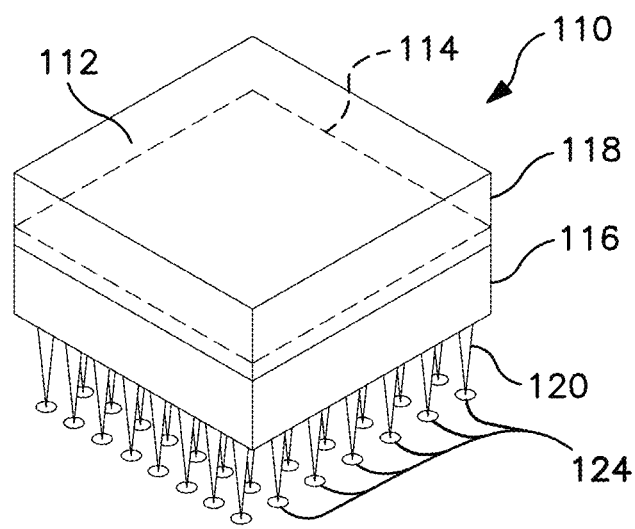

FIGS. 14A and 14B are perspective views of a device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120. A release liner 122 may be removed prior to use of the device to expose microneedles 120.

A formulation including one or more agents may be retained within the reservoir 112. Materials suitable for use as impermeable backing layer 114 may include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 114 and the base of the microneedle array 116, provides a storage structure in which to retain the suspension of agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the base upon which the microneedles are located. According to another embodiment, the reservoir may be separate and removably connectable to the microneedle array or in fluid communication with the microneedle array, for instance via appropriate tubing, leur locks, etc.

The device may include one or a plurality of reservoirs for storing agents to be delivered. For instance, the device may include a single reservoir that stores a single agent or multiple agent formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

The reservoir may be in fluid communication with one or more microneedles of the transdermal device, and the microneedles may define a structure (e.g., a central or lateral bore) to allow transport of delivered agents beneath the barrier layer.

Figure 15:
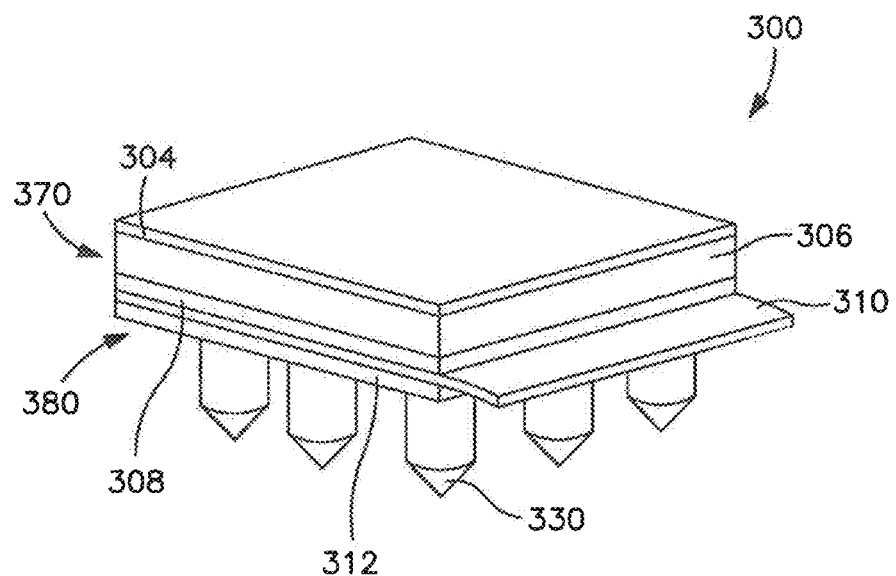
FIG. 15 is a perspective view of one embodiment of a transdermal patch prior to delivery of a drug compound.
Figure 16:
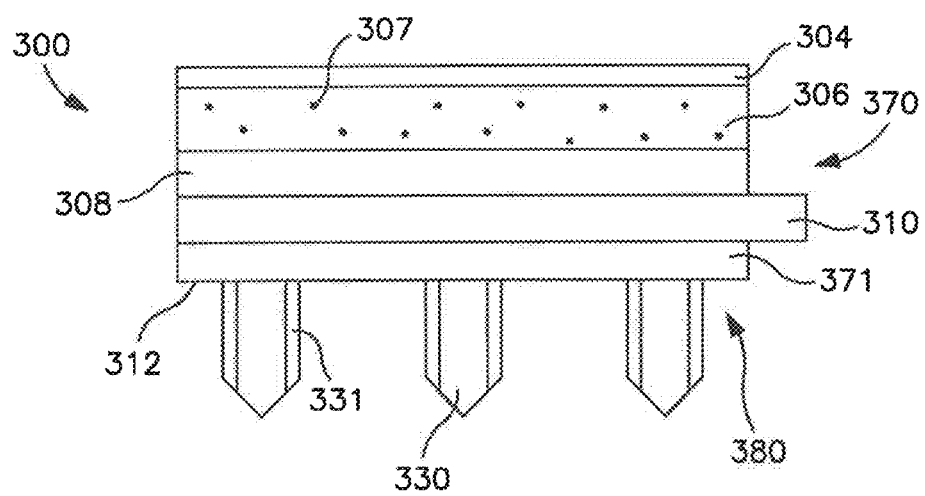
FIG. 16 is a front view of the patch of FIG. 15.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 15-20, one embodiment of a release member is shown that is configured to be detached from a transdermal patch to initiate the flow of a drug compound. More particularly, FIGS. 15-16 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Referring to FIGS. 15-16, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 15-16) that extends at least partly beyond the perimeter of the patch 300 to facilitate the ability of a user to grab onto the member and pull it in the desired direction. In its "inactive" configuration as shown in FIGS. 15-16, the drug delivery assembly 370 of the patch 300 securely retains a drug compound 307 so that it does not flow to any significant extent into the microneedles 330. The patch may be "activated" by simply applying a force to the release member so that it is detached from the patch.

Figure 17:
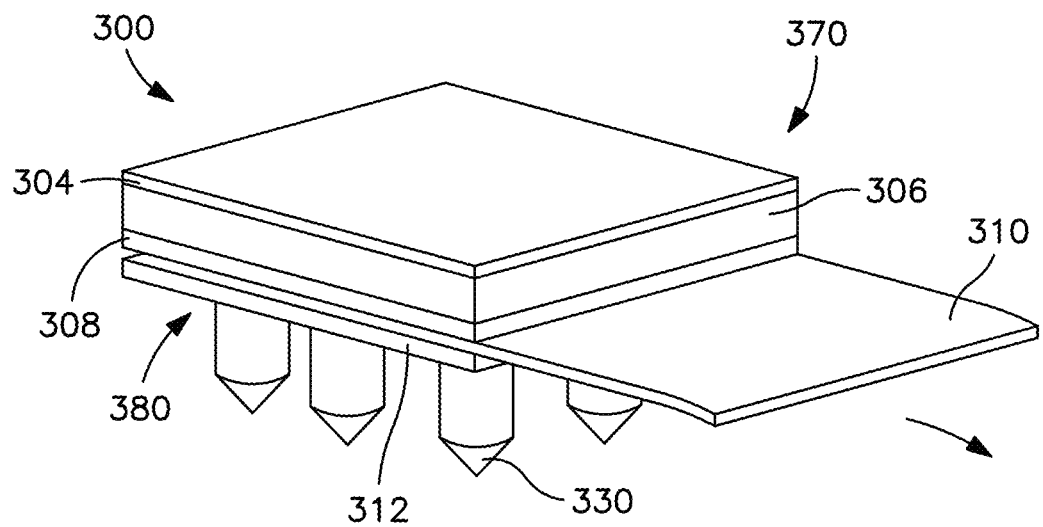
FIG. 17 is a perspective view of the patch of FIG. 15 in which the release member is partially withdrawn from the patch.
Figure 18:
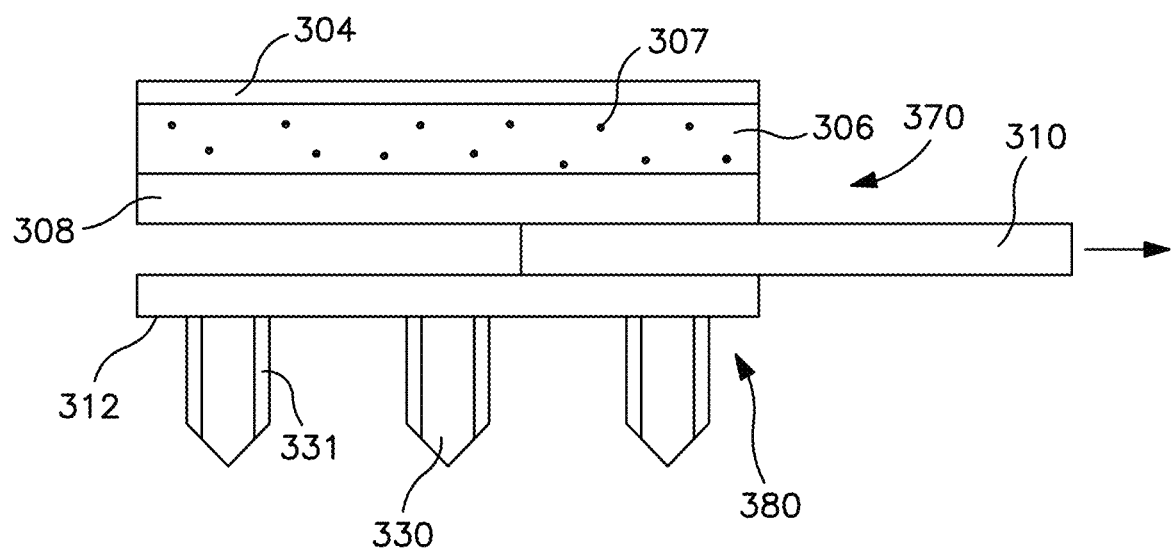
FIG. 18 is a front view of the patch of FIG. 15.
Figure 19:
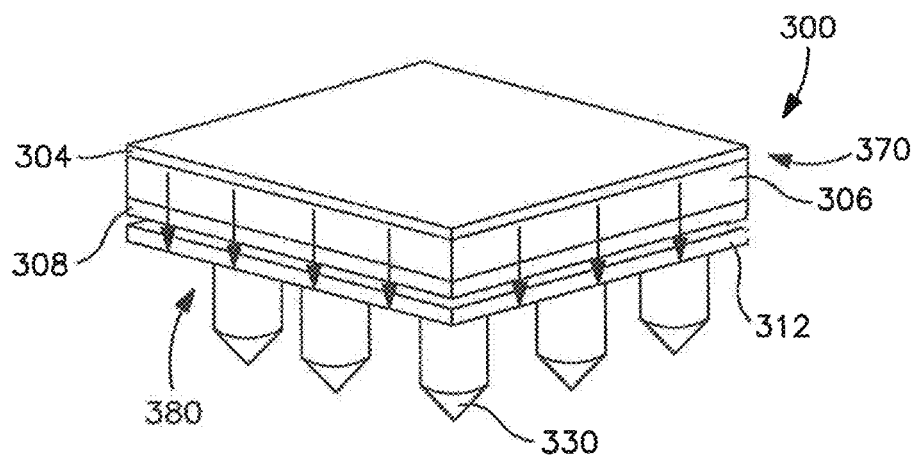
FIG. 19 is a perspective view of the transdermal patch of FIG. 15 after removal of the release member and during use.
Figure 20:
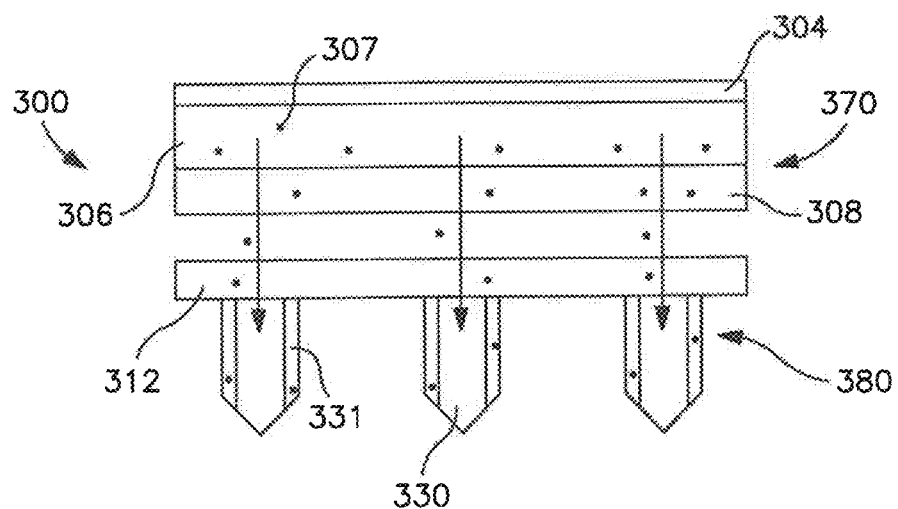
FIG. 20 is a front view of the patch of FIG. 19.

Referring to FIGS. 17-18, one embodiment for activating the patch 300 is shown in which the release member 310 is pulled in a longitudinal direction. The entire release member 310 may be removed as shown in FIGS. 19-20, or it may simply be partially detached as shown in FIGS. 17-18. In either case, however, the seal previously formed between the release member 310 and the aperture (not shown) of the support 312 is broken. In this manner, a drug compound 107 may begin to flow from the drug delivery assembly 170 and into the channels 131 of the microneedles 130 via the support 112. An exemplary illustration of how the drug compound 307 flows from the reservoir 306 and into the channels 331 is shown in FIGS. 19-20. Notably, the flow of the drug compound 307 is passively initiated and does not require any active displacement mechanisms (e.g., pumps).

In the embodiments shown in FIGS. 15-20, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 21:
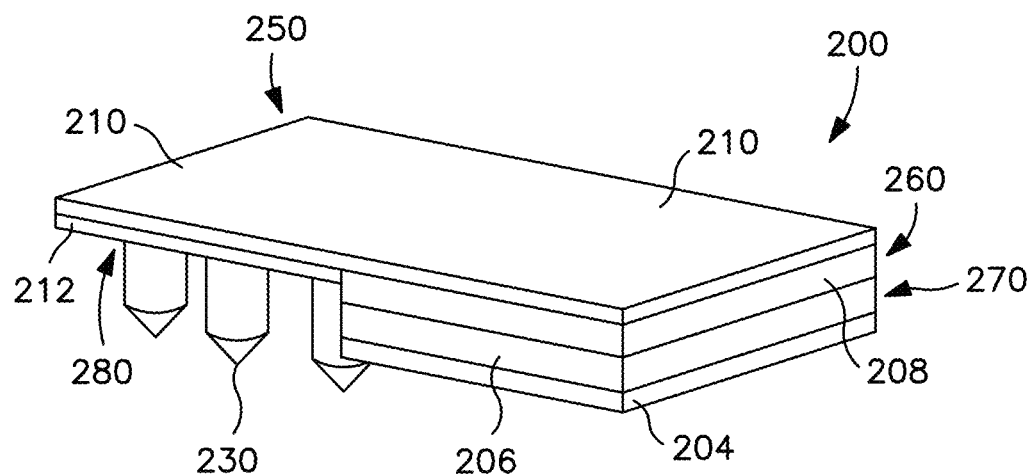
FIG. 21 is a perspective view of another embodiment of a transdermal patch prior to delivery of a drug compound.
Figure 22:
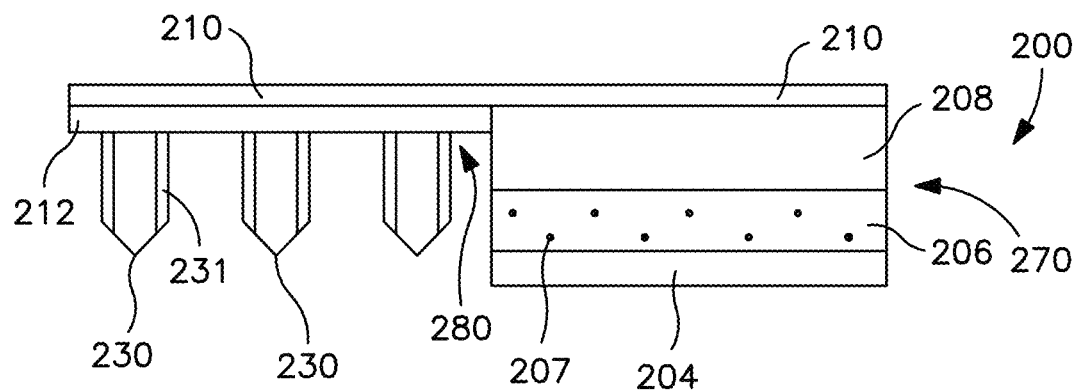
FIG. 22 is a front view of the patch of FIG. 21.

Referring to FIGS. 21-26, for example, one particular embodiment of a patch 200 is shown. FIGS. 21-22 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

Figure 23:
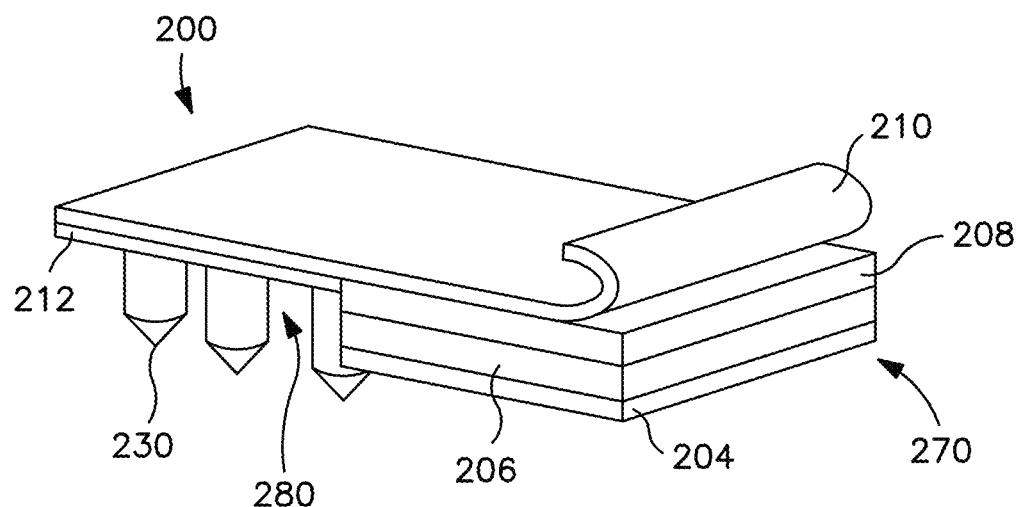
FIG. 23 is a perspective view of the patch of FIG. 21 in which the release member is partially peeled away from the patch.
Figure 24:
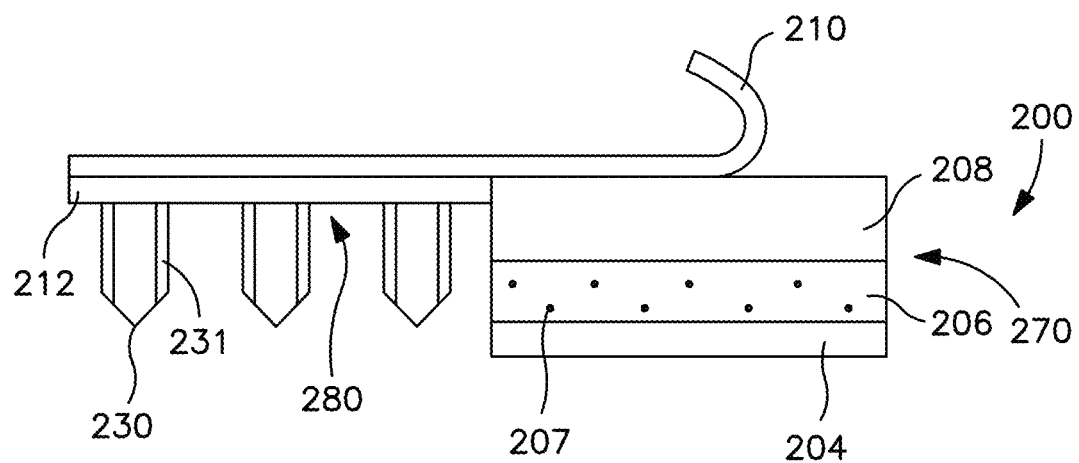
FIG. 24 is a front view of the patch of FIG. 23.
Figure 25:
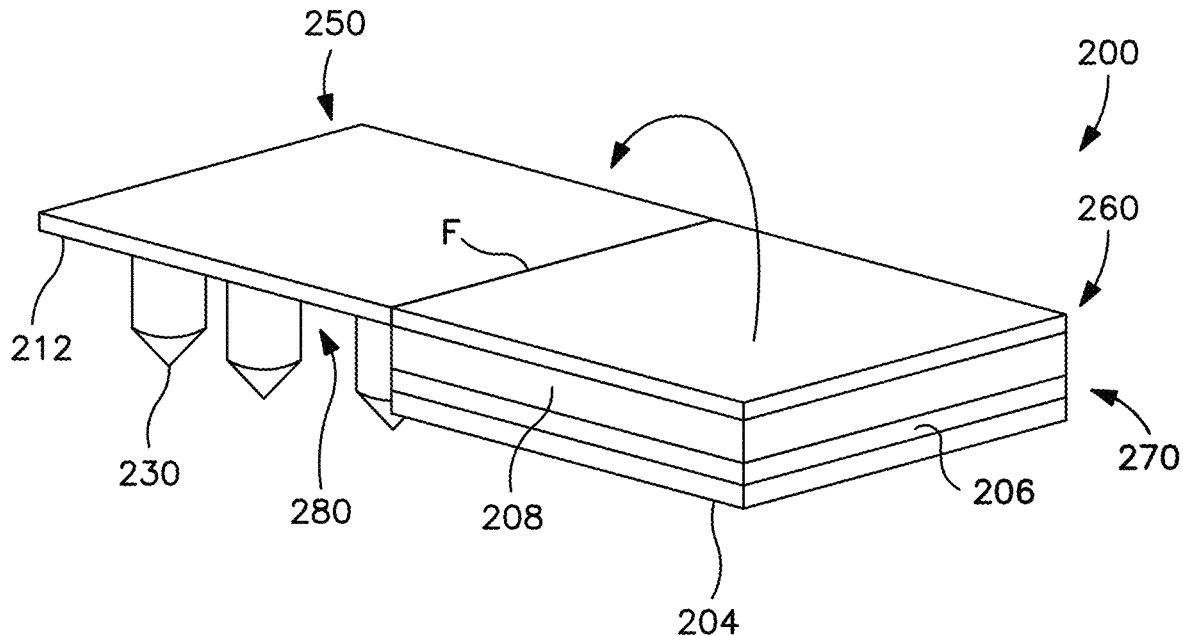
FIG. 25 is a perspective view of the patch of FIG. 21 in which the release member is completely peeled away from the patch.
Figure 26:
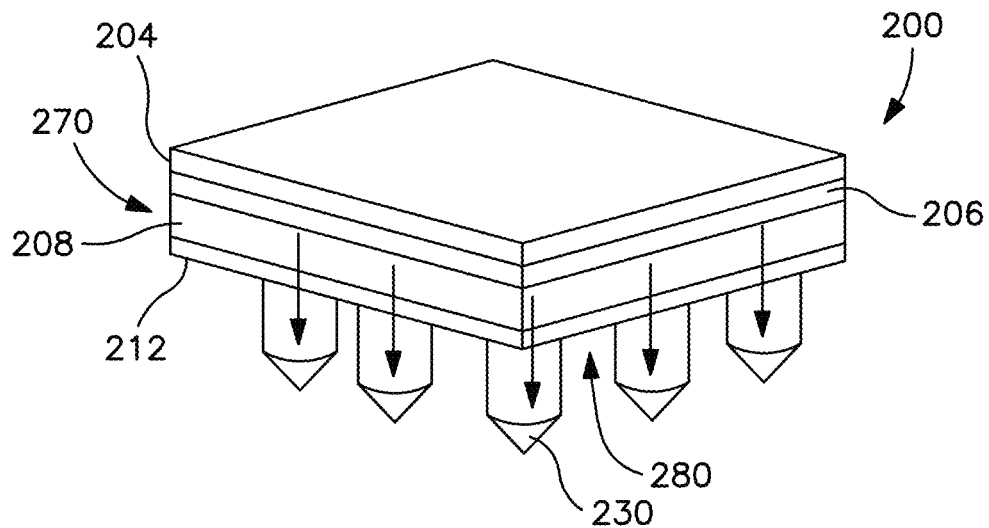
FIG. 26 is a perspective view of the transdermal patch of FIG. 21 after removal of the release member and during use.

In this embodiment, the support 212 and the rate control membrane 208 are initially positioned horizontally adjacent to each other, and a release member 210 extends over the support 212 and the rate control member 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 21-22, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 23-24, to break the seal previously formed between the release member 210 and the aperture (not shown) of the support 212. Thereafter, the second section 260 may be folded about a fold line "F" as shown by the directional arrow in FIG. 25 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 26).

The device may deliver an agent at a rate so as to be therapeutically useful. In accord with this goal, a transdermal device may include a housing with microelectronics and other micro-machined structures to control the rate of delivery either according to a preprogrammed schedule or through active interface with the patient, a healthcare professional, or a biosensor. The device may include a material at a surface having a predetermined degradation rate, so as to control release of an agent contained within the device. A delivery rate may be controlled by manipulating a variety of factors, including the characteristics of the formulation to be delivered (e.g., viscosity, electric charge, and/or chemical composition); the dimensions of each device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with the device may include micropumps, microvalves, and positioners. For instance, a microprocessor may be programmed to control a pump or valve, thereby controlling the rate of delivery.

Flow of an agent through the device may occur based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a microneedle, and/or a substrate adjacent a microneedle, to create a convective flow which carries oppositely charged ionic species and/or neutral molecules toward or into the delivery site.

Flow of an agent may be manipulated by selection of the material forming the microneedle surface. For example, one or more large grooves adjacent the microneedle surface of the device may be used to direct the passage of drug, particularly in a liquid state. Alternatively, the physical surface properties of the device may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

Agents as may be delivered by the device may be intended for the local area near the device or may be intended for wider distribution. For instance, in one embodiment, the device may deliver agents for pain management or inflammation management to a local area around a joint, for instance in treatment of osteoarthritis or rheumatoid arthritis.

The nanotopography of the device may improve delivery of agents while minimizing foreign body and immune response. This may prove particularly beneficial when considering delivery of oligonucleotides and other therapeutics to the nuclear envelope. In the past, delivery of materials (e.g., plasmids, siRNA, RNAi, and so forth), to the nuclear envelope has proven problematic because even when endocytosis is achieved, proper endosomal delivery to the nuclear envelope has proven difficult, most likely due to foreign body and immune response. Once in the cytoplasm, delivered material is often recycled via late endosomes or degraded in the lysosome. By use of disclosed devices, interaction of a microneedle with the ECM may prevent foreign body response within a cell following endocytosis and encourage delivery of the materials to the nucleus.

Delivery of protein therapeutics has likewise proven problematic in the past. For instance, delivery of high molecular weight agents such as protein therapeutics has proven difficult for transdermal delivery routes due to the natural barriers of the skin. The presence of the nanotopography on a microneedle may beneficially affect the thermodynamics of the ECM and improve efficiency of delivery and uptake of protein therapeutics. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. For instance, the presence of the device in or near the stratum granulosum may open tight junctions and allow paracellular transport of high molecular weight agents. In one embodiment, the device may be utilized in transdermal delivery of high molecular weight agents (e.g., agents defining a molecular weight greater than about 400 Da, greater than about 10 kDa, greater than about 20 kDa, or greater than about 100 kDa, e.g., about 150 kDa). Additionally, variation of the surface area to volume ratio of the device may be utilized to alter protein adsorption at the surface of the device, which may in turn alter delivery and cellular uptake of materials. Thus, deliver of a particular material may be optimized through optimization of the surface area/volume ratio of the device.

Even when considering delivery of small molecular weight agents, the device may provide increased efficiency and improved uptake due to interaction of the device with components of the dermal connective tissue and accompanying decrease in foreign body response and improvement in localized chemical potential of the area.

Of course, devices are not limited to targeted delivery of agents. Systemic deliver of agents is also encompassed herein as is withdrawal of an agent from a subject via the device.

There is no particular limitation to agents as may be delivered by use of the device. Agents may include proteinaceous agents such as insulin, immunoglobulins (e.g., IgG, IgM, IgA, IgE), TNF-α, antiviral medications, and so forth; polynucleotide agents including plasmids, siRNA, RNAi, nucleoside anticancer drugs, vaccines, and so forth; and small molecule agents such as alkaloids, glycosides, phenols, and so forth. Agents may include anti-infection agents, hormones, drugs regulating cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143 entitled "Method of Intradermally Injecting Substances", the entire content of which is incorporated herein by reference. Vaccine formulations may include an antigen or antigenic composition capable of eliciting an immune response against a human pathogen or from other viral pathogens.

In one preferred embodiment, the device may be utilized in treatment of a chronic condition, such as rheumatoid arthritis, to deliver a steady flow of an agent, to a subject in need thereof. RA drugs that may be delivered via disclosed devices may include symptom suppression compounds, such as analgesics and anti-inflammatory drugs including both steroidal and non-steroidal anti-inflammatory drugs (NSAID), as well as disease-modifying antirheumatic drugs (DMARDs).

The device may include and deliver symptom suppression compounds, such as analgesics and anti-inflammatory drugs, as well as DMARD compounds, including biological DMARDs. While not wishing to be bound to any particular theory, it is understood that the nanometer-scale structures fabricated on the surface of the device improve deliver of the compounds across the dermal barrier. Through utilization of the device, RA drugs may be delivered at a steady concentration over a sustained period. The device may prevent the initial burst of concentration common when utilizing previously known methods for delivery of RA drugs, including oral delivery and injection.

The present disclosure may be further understood with reference to the Examples provided below.

Example 1

Several different molds were prepared using photolithography techniques similar to those employed in the design and manufacture of electrical circuits. Individual process steps are generally known in the art and have been described.

Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 µC/cm$^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm)

He, 22 sccm $CF_4$, 20 sccm $C_4F_8$ at 4 mTorr, 400 W coil, 200 W RIE and a DC Bias of 404-411 V.

Following, a silicon oxide etch was carried out with an STS silicon oxide etch (SOE). Etch time was 2 minutes utilizing 20 sccm $Cl_2$ and 5 sccm Ar at 5 mTorr, 600 W coil, 50 W RIE and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre® 6 nanoimprinter was used to form nanopatterns on a variety of polymer film substrates. External water was used as coolant. The UV module utilized a single pulsed lamp at a wave length of between 200 and 1000 nanometers at 1.8 W/cm². A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Figure 27A:
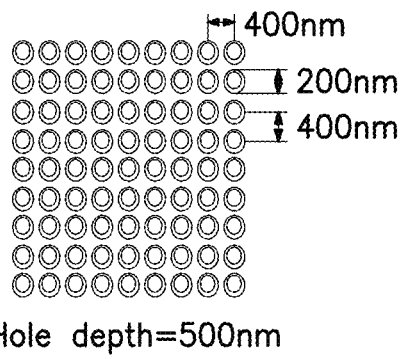
Figure 27A:
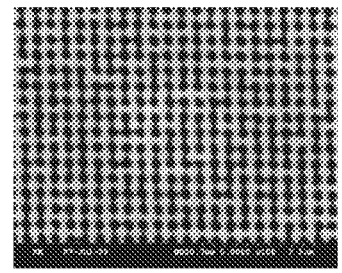
Figure 27B:
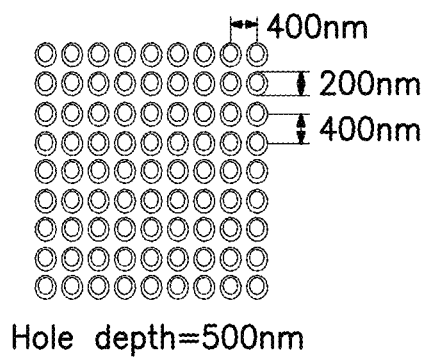
Figure 27B:
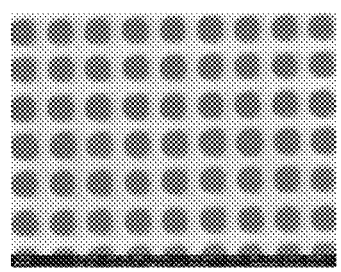
Figure 27C:
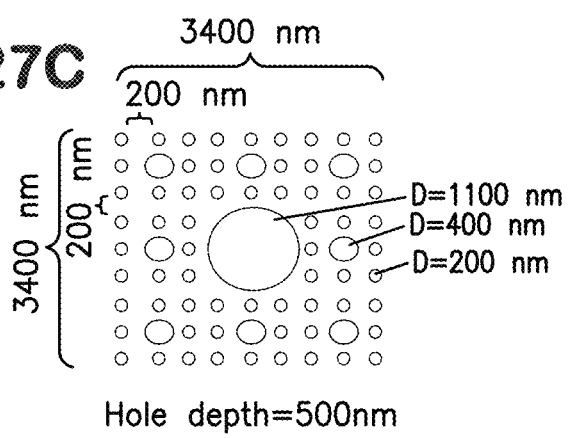
Figure 27C:
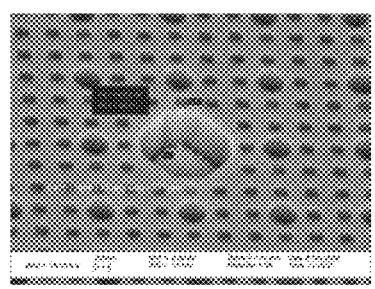
Figure 27D:
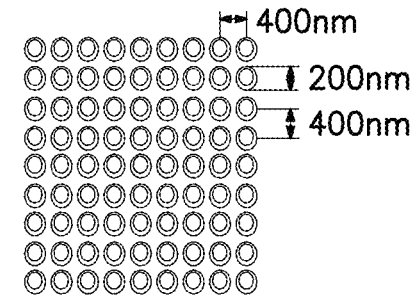
Figure 27D:
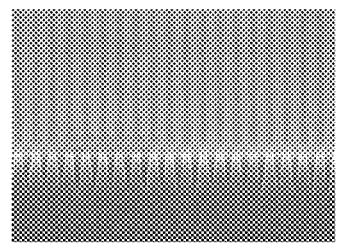
Figure 29A:
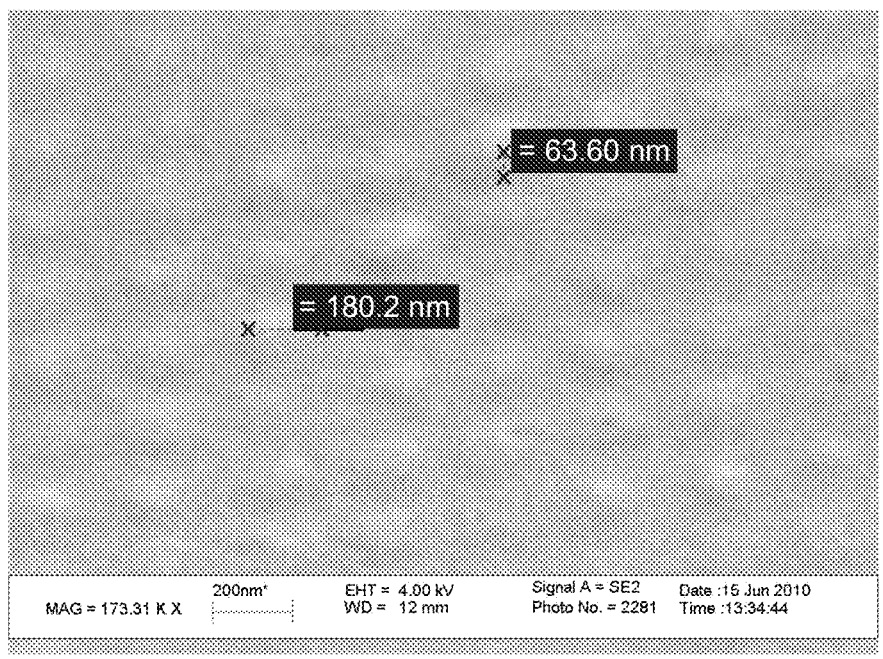
FIGS. 29A and 29B are two SEM of a film including another nanopatterned surface.
Figure 29B:
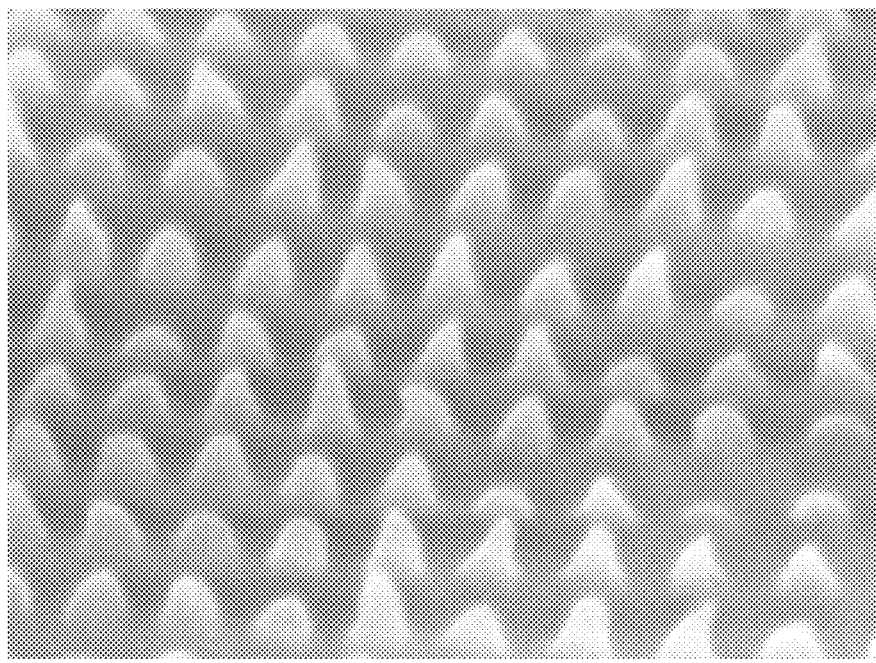
Figure 30:
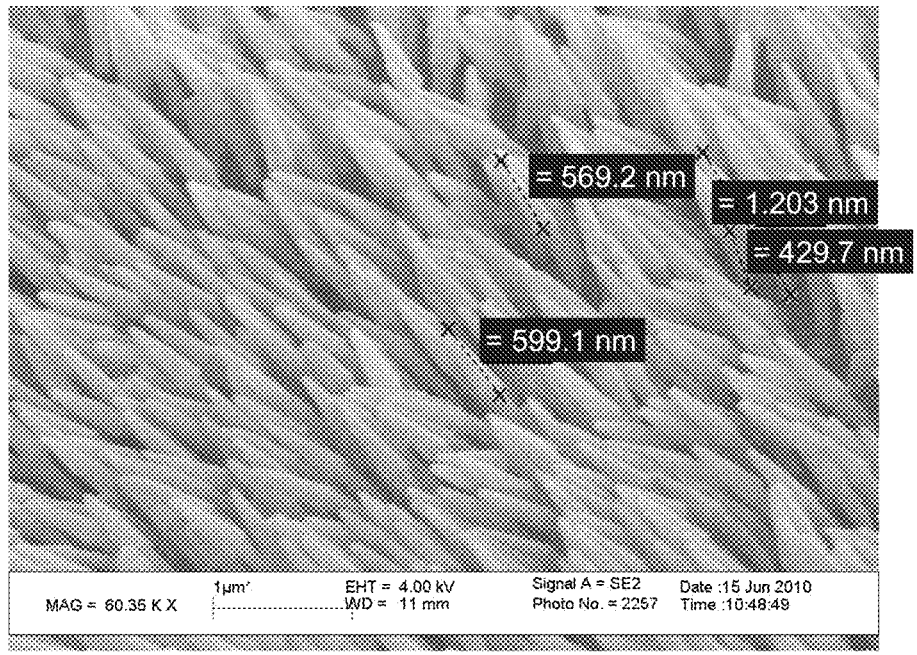
FIG. 30 is an SEM of a film including another nanopatterned surface.
Figure 31:
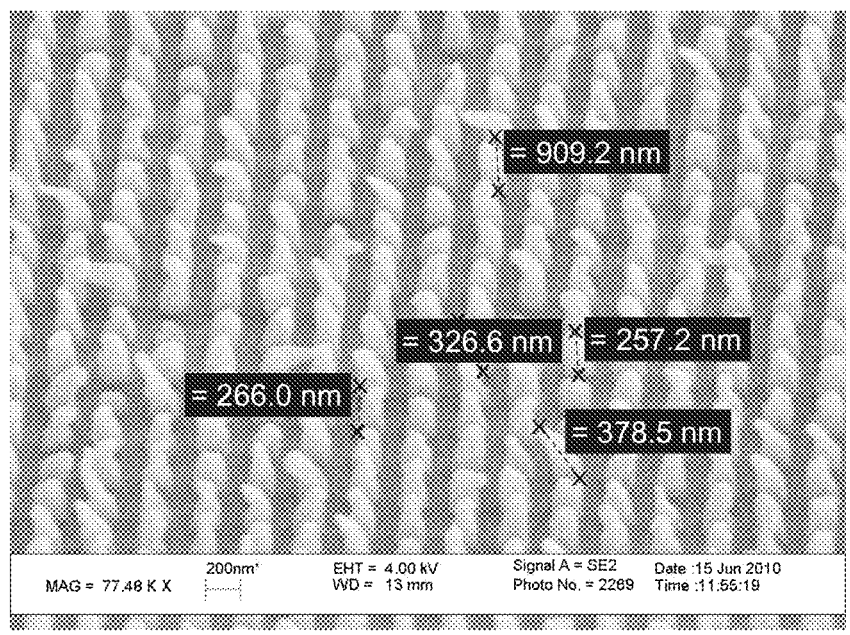
FIG. 31 is an SEM of a film including another nanopatterned surface.
Figure 32:
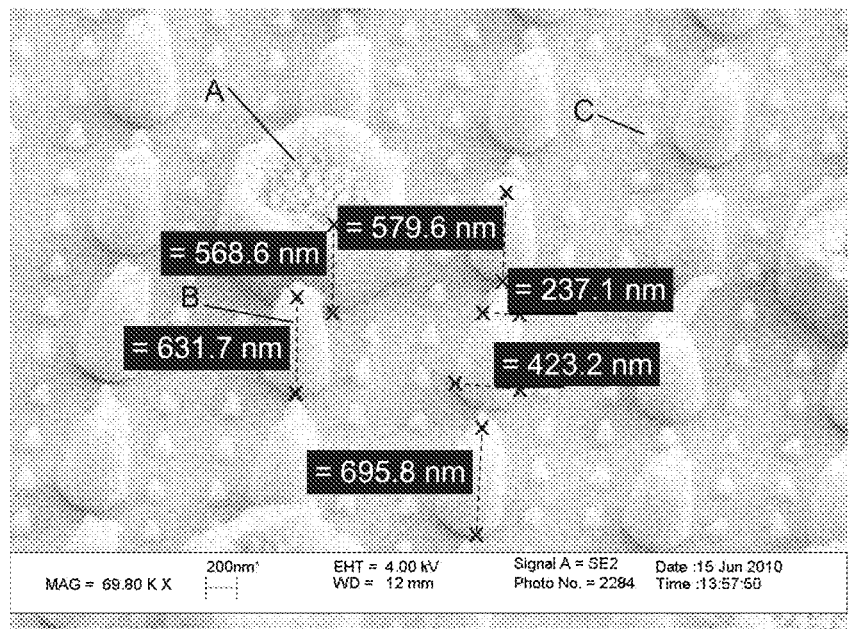
FIG. 32 is an SEM of a film including another nanopatterned surface.
Figure 33:
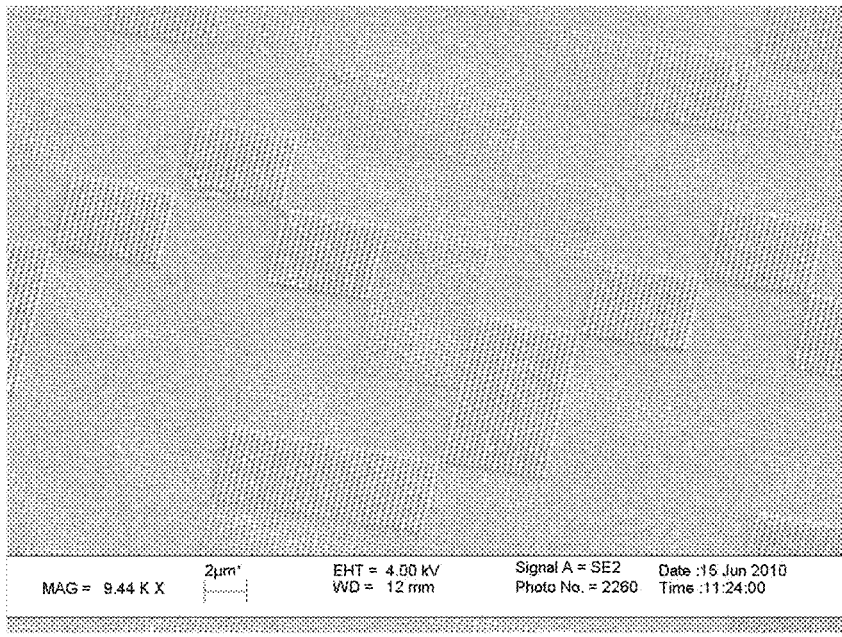
FIG. 33 is an SEM of a film including another nanopatterned surface.
Figure 34:
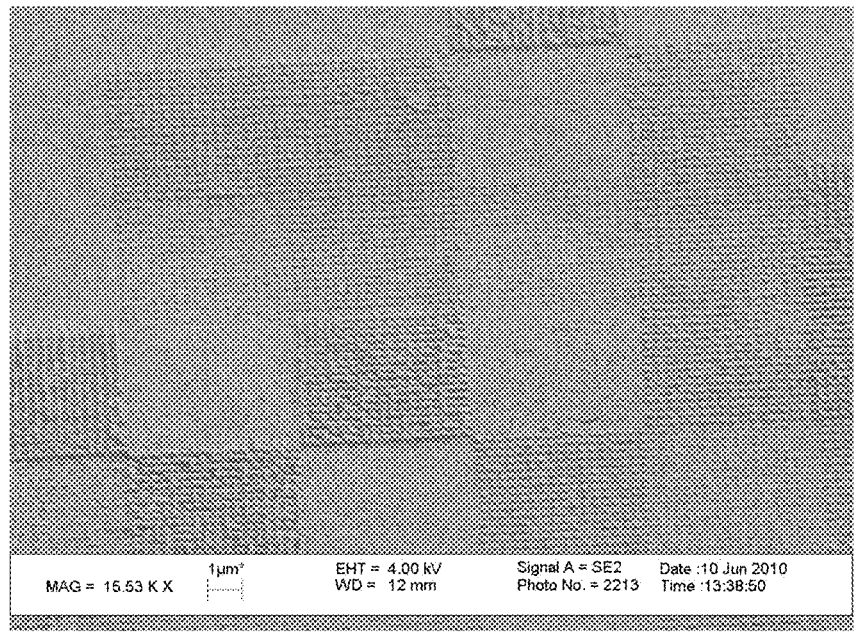
FIG. 34 is an SEM of a film including another nanopatterned surface.
Figure 35:
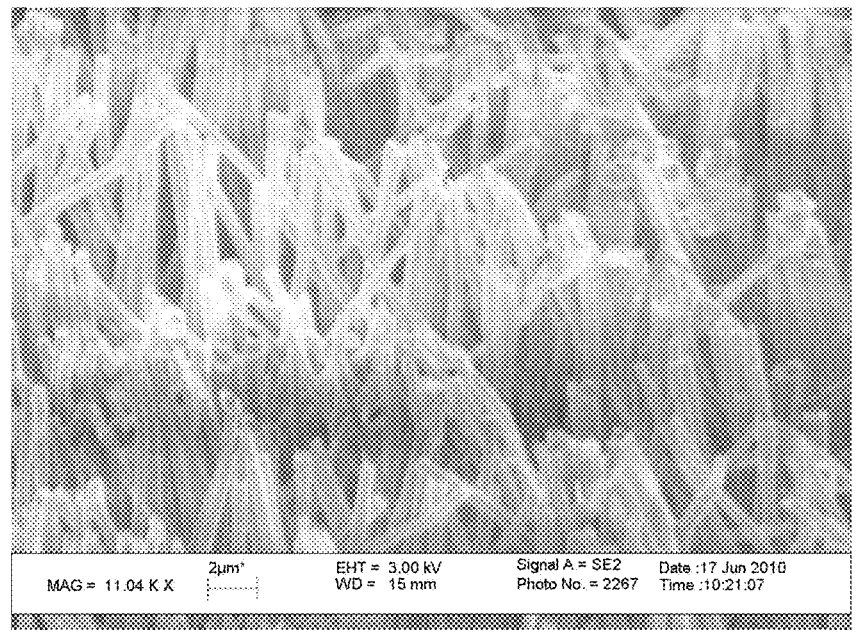
FIG. 35 is an SEM of a film including another nanopatterned surface.
Figure 36:
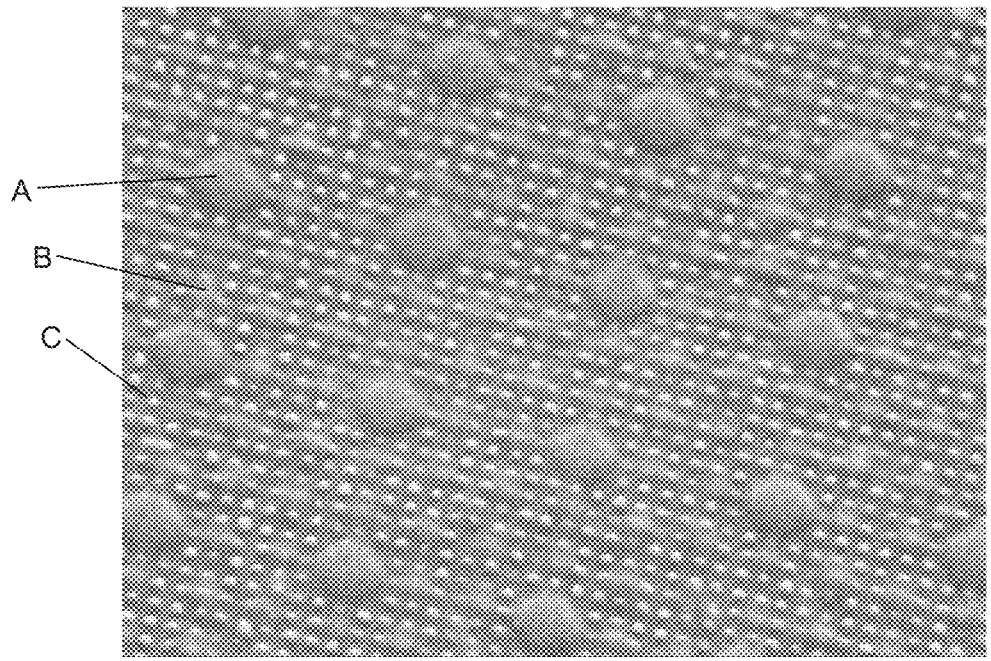
FIG. 36 is an SEM of a film including another nanopatterned surface.

Several different nanotopography patterns were formed, schematic representations of which are illustrated in FIGS. 27A-27E. The nanotopography pattern illustrated in FIG. 27E was a surface of a flat substrate purchased from NTT Advanced Technology of Tokyo, Japan. The patterns were designated DN1 (FIG. 27A), DN2 (FIG. 27B), DN3 (FIG. 27C), DN4 (FIG. 27D) and NTTAT2 (FIG. 27E). SEM images of the molds are shown in FIGS. 27A, 27B, and 27C, and images of the films are shown in FIGS. 27D and 27E. FIG. 11 illustrates a nanopatterned film formed by use of the mold of FIG. 27A (DN1). In this particular film, the polymer features were drawn by temperature variation as previously discussed. The surface roughness of the pattern of FIG. 27E was found to be 34 nanometers.

The pattern illustrated in FIGS. 10C and 10D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 μm. Pillars 62 were 500 nanometers in height and 200 nanometers in diameter and a center-to-center spacing of 250 nanometers.

The nanoimprinting process conditions used with polypropylene films are provided below in Table 2.

TABLE 2

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

Films were formed as described in Example 1 including various different patterns and formed of either polystyrene (PS) or polypropylene (PP). The underlying substrate varied in thickness. Patterns utilized were DN2, DN3, or DN4 utilizing formation processes as described in Example 1. The pattern molds were varied with regard to hole depth and feature spacing to form a variety of differently-sized features having the designated patterns. Sample no. 8 (designated BB1) was formed by use of a 0.6 m millipore polycarbonate filter as a mold. A 25 μm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are shown in FIGS. 28-36 and the characteristics of the formed films are summarized in Table 3, below.

TABLE 3

| Sample No. | FIG. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 1 | 28 | DN3 | PS | 75 | A | 1100 nm | 520 nm | 0.47 | 150 | 2.0 | 100° |
|   |   |   |   |   | B | 400 nm | 560 nm | 1.4 |   |   |   |
|   |   |   |   |   | C | 200 nm | 680 nm | 3.4 |   |   |   |
| 2 | 29A, 29B | DN2 | PP | 5.0 | n/a | 200 nm | 100 nm | 0.5 | 16 | 2.15 | 91° |
| 3 | 30 | DN2 | PS | 75 | n/a | 200 nm | 1.0 μm | 5 | 64 | 2.2 | 110° |
| 4 | 31 | DN2 | PP | 25.4 | n/a | 200 nm | 300 nm | 1.5 | 38 | 1.94 | 118° |
| 5 | 32 | DN3 | PS | 75 | A | 1100 nm | 570 nm | 0.52 | 21.1 | 1.98 | 100° |
|   |   |   |   |   | B | 400 nm | 635 nm | 1.6 |   |   |   |
|   |   |   |   |   | C | 200 nm | — | — |   |   |   |
| 6 | 33 | DN4 | PS | 75 | n/a | 200 nm | — | — | 30.6 | 2.04 | 80° |
| 7 | 34 | DN4 | PP | 25.4 | n/a | 200 nm | — | — | 21.4 | 2.07 | 112° |

TABLE 3-continued

| Sample No. | FIG. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 8 | 35 | BB1 | PP | 25.4 | n/a | 600 nm | 18 μm | 30 | 820 | 2.17 | 110° |
| 9 | 36 | DN3 | PP | 5 | A | 1100 nm | 165 nm | 0.15 | 50 | 2.13 | — |
|   |    |     |    |   | B | 400 nm | 80 nm | 0.2 |   |   |   |
|   |    |     |    |   | C | 200 nm | 34 nm | 0.17 |   |   |   |

[1]Pattern Features as shown on the figures.
[2]Cross sectional dimension values were derived from the mold and equated as an approximation of the maximum dimension of the structure, although it should be understood that the actual dimension of any given individual structure may vary slightly as may be seen in the figures.
[3]Feature heights are provided as the average of several individually determined feature heights For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from μMasch. The cantilever had a resonant frequency of 170 kHz, a spring constant of 40 N/m, a length of 230±5 μm, a width of 40±3 μm, and a thickness of 7.0±0.5 μm. The probe tip was an n-type phosphorous-doped silicon probe, with a typical probe tip radius of 10 nanometers, a full tip cone angle of 40°, a total tip height of 20-25 μm, and a bulk resistivity 0.01-0.05 ohm-cm.

The surface roughness value given in Table 3 is the arithmetical mean height of the surface areal roughness parameter as defined in the ISO 25178 series.

The Fractal Dimension was calculated for the different angles by analyzing the Fourier amplitude spectrum, for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log-log curves. The reported fractal dimension is the average for all directions.

The fractal dimension may also be evaluated from 2D Fourier spectra by application of the Log Log function. If the surface is fractal the Log Log graph should be highly linear, with at negative slope (see, e.g., Fractal Surfaces, John C. Russ, Springer-Verlag New York, LLC, July, 2008).

Example 3

An array of microneedles including an overlaid film defining a nanopatterned surface was formed. Initially, an array of microneedles was formed on a silicon wafer via a photolithography process. Each needle included two oppositely placed side channels, aligned with one through-die hole in the base of the needle.

Microneedles were formed according to a typical micromachining process on a silicon based wafer. The wafers were layered with resist and/or oxide layers followed by selective etching (oxide etching, DRIE etching, iso etching), resist stripping, oxide stripping, and lithography techniques (e.g., iso lithography, hole lithography, slit lithography) according to standard methods to form the array of microneedles.

Following formation of the microneedle array, a 5 μm polypropylene film including a DN2 pattern formed thereon as described in Example 1, the characteristics of which are described at sample 2 in Table 3, was laid over the microneedle array. The wafer/film structure was held on a heated vacuum box (3 inches H₂O vacuum) at elevated temperature (130° C.) for a period of one hour to gently pull the film over the surface of the microneedles while maintaining the nanopatterned surface of the film.

Figure 37:
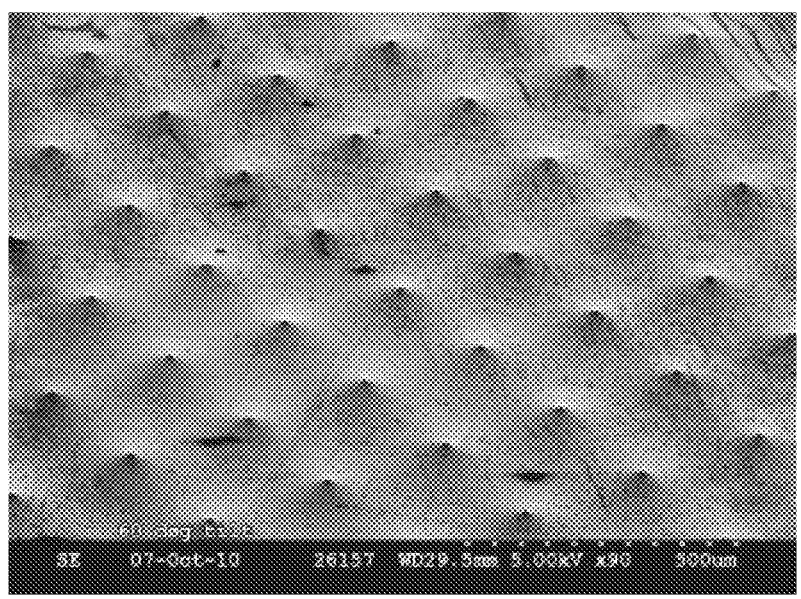
FIG. 37 is an array of microneedles including a film draped on the microneedles, the film defining a pattern of nanostructures thereon.
Figure 38:
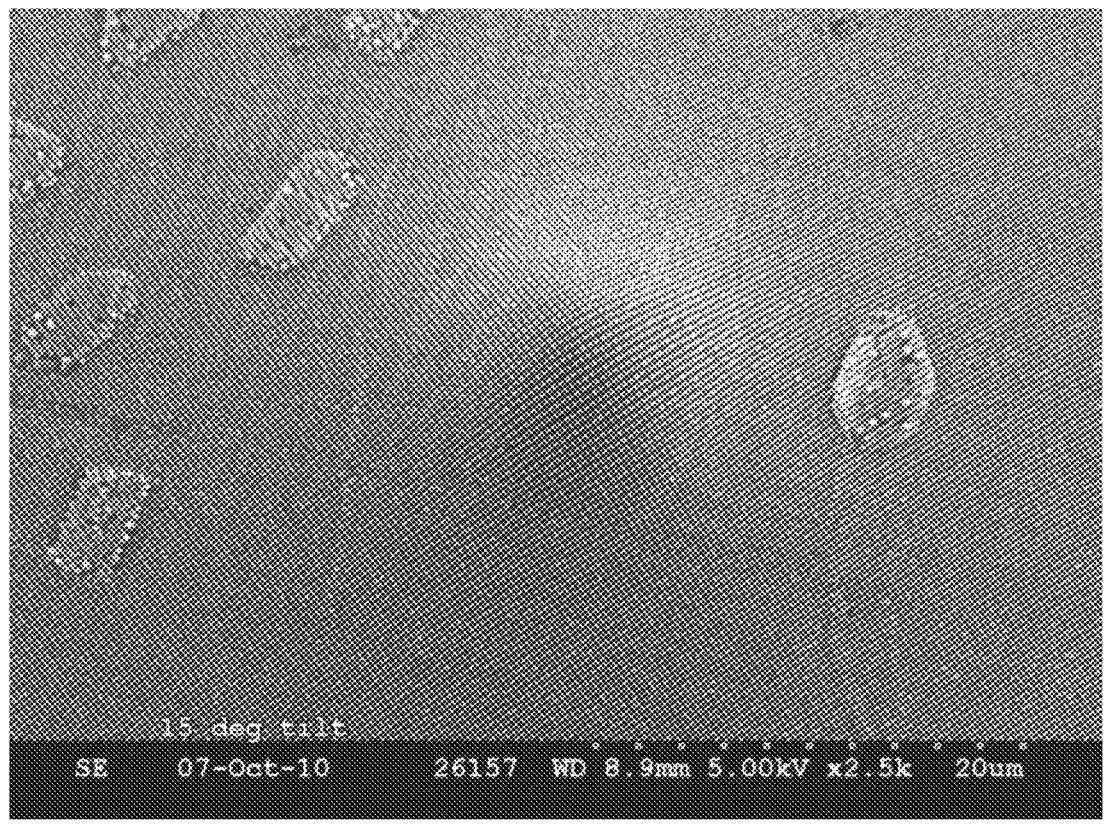
FIG. 38 is a single microneedle of the array of FIG. 37.

FIG. 37 illustrates the film over the top of the array of microneedles, and FIG. 38 is a closer view of a single needle of the array including the nanopatterned film overlaying the top of the needle.

Example 4

Transdermal patches including microneedle arrays formed as described in Example 3 were formed. Patches were formed with either a DN2 pattern or a DN3 pattern on the microneedle array.

The films defining the patterns that were applied to the microneedles are described in Table 4, below. Film 1 is equivalent to sample no. 2 of Table 3 and Film 2 is equivalent to sample no. 9 of Table 3.

TABLE 4

| Property | Film 1 | Film 2 |
|---|---|---|
| Pattern | DN2 | DN3 |
| Material | polypropylene | polypropylene |
| Film Thickness | 5 micrometers | 5 micrometers |
| Height of structures | 100 nm | 165 nm, 80 nm, 34 nm |
| Aspect ratio of structures | 0.5 | 0.18 |
| Average Surface Roughness $R_A$ | 16 nm | 50 nm |
| Fractal Dimension | 2.15 | 2.13 |

Control patches were also formed that had no pattern formed on the film and subsequently applied to the array of microneedles. Transdermal and subcutaneous formulations of etanercept (Enbrel®) were prepared according to instructions from the drug supplier. The subcutaneous dose formulation (for the positive control) was prepared to facilitate a 4 mg/kg subcutaneous drug dose. The concentration of Enbrel® for transdermal delivery was adjusted such that an intended dosing of 200 mg/kg was achieved in a 24 hr period.

A total of 10 BALB/C mice (assigned designations #1-#10) were used in the study, 8 were transdermally dosed with Enbrel® (group 1) and 2 were subcutaneously dosed with Enbrel® (group 2) as described in Table 5, below. The transdermal patches were applied to shaved skin areas and holes formed near the microneedle tips upon application of the patch to the skin.

TABLE 5

| Group No. | Test Article | Drug | Dose Route | Dose Level | Dose volume | Blood Collection Time Points | Animal Number |
|---|---|---|---|---|---|---|---|
| 1 | Transdermal patch | Enbrel ® | Transdermal | 5 mg/subject | 0.2 ml | Pre-patch<br>0.5 h<br>2 h<br>6 h<br>24 h<br>72 h | #1, #5<br>#2, #6<br>#3, #7<br>#4, #8<br>#2, #6<br>#3, #7 |
| 2 | subcutaneous delivery | Enbrel ® | Subcutaneous | 4 mg/kg | 0.1 ml | 24 h | #9, #10 |

Transdermal patches used included both those defining a nanotopography on the surface (DN2 and DN3 patterns, as described above), as well as patches with no pattern of nanotopography.

Samples of whole blood were collected at the time points indicated in Table 5. Approximately 100 to 200 μl of blood was taken via mandibular bleeding and then centrifuged at approximately 1300 rpm for 10 minutes in a refrigerated centrifuge (set at 4° C.). The resulting serum was aspirated and transferred within 30 minutes of blood collection/centrifugation to appropriately labeled tubes. The tubes were frozen and stored in the dark at <−70° C. until they were analyzed for levels of Enbrel® using Human sTNF-receptor ELISA kit (R&D Systems cat #DRT200). The space time between two blood samplings on the same subject was 24 hours, to prevent unnecessary stress placed on the subject.

Figure 39:
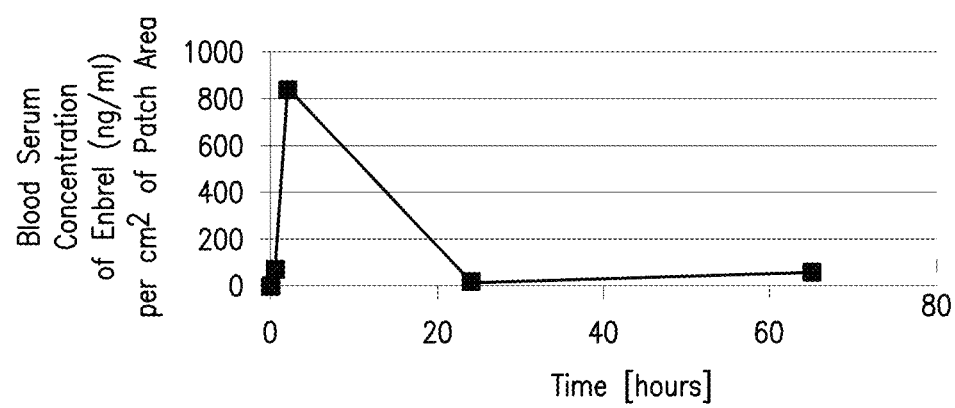
FIG. 39 graphically illustrates the PK profile of a protein therapeutic delivered with a device as illustrated in FIG. 37.

FIG. 39 graphically illustrates the average PK profile of the transdermal patches that defined nanotopography thereon. An average of the results for all nanotopography-including patches was used to represent the overall effect of incorporating nanotopography in conjunction with a microneedle transdermal patch. As may be seen, the blood serum level rose rapidly to over 800 ng/mL/cm$^2$ of patch area within the first two hours of attachment. Following, the blood serum level gradually declined to negligible within 24 hours of attachment. The data used to develop FIG. 39 is provided below in Table 6.

TABLE 6

| Time (hr) | Blood serum concentration (ng/ml) |
|---|---|
| 0 | 0 |
| 0.5 | 192.1 |
| 2 | 249.25 |
| 6 | 24.4 |
| 24 | 7.2 |
| 65 | 4.0875 |

Figure 40A:
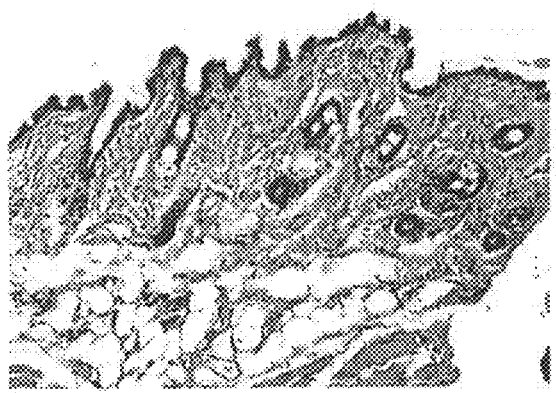
FIGS. 40A and 40B are cross sectional images of skin following transdermal delivery of a protein therapeutic across the skin.
Figure 40B:
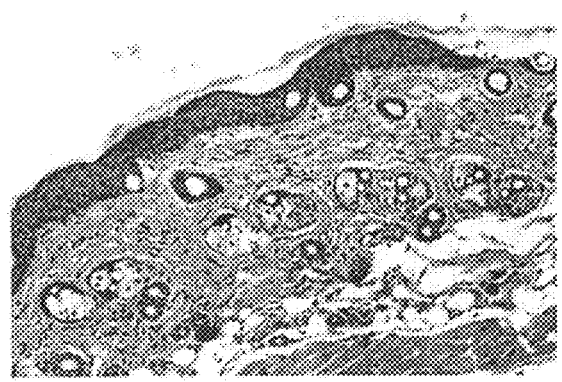

FIGS. 40A and 40B illustrate electron microscopy cross sectional views of the skin that was held in contact with the patches. The images were taken after the patches were removed (72 hours post-attachment). The sample of FIG. 40A was in contact with a patch including a nanotopography on the surface. Specifically, a DN2 pattern, as described above, was formed on the surface of the patch. The sample of FIG. 40B was held in contact with a transdermal patch that did not define a pattern of nanotopography on the surface. As may be seen, the sample of FIG. 40B shows signs of inflammation and a high density of macrophage presence.

Example 5

Transdermal patches including microneedle arrays formed as described in Example 3 were formed. Patches were formed with either a DN2 pattern or a DN3 pattern on the microneedle array as described in Table 4 of Example 4. Control patches were also formed that had no pattern formed on the film subsequently applied to the array of microneedles. Transdermal and subcutaneous formulations of etanercept (Enbrel®) were prepared according to instructions from the drug supplier.

Figure 41:
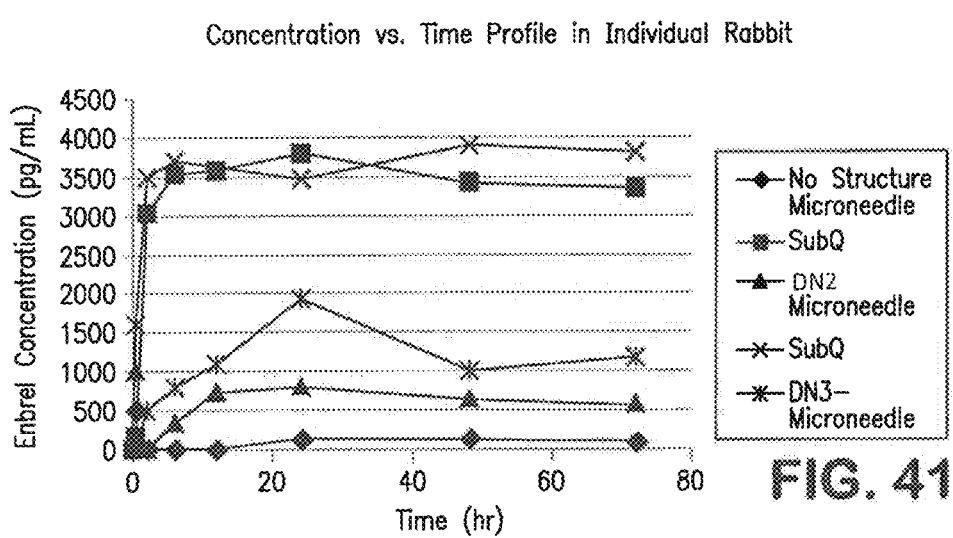
FIG. 41 graphically illustrates the blood serum concentration of a protein therapeutic delivered with a device as described herein.

Test subjects (rabbits) were transdermally dosed with Enbrel® or were subcutaneously (SubQ) dosed with Enbrel®. Results are illustrated graphically in FIG. 41, which provides the blood serum concentration in pg/ml as a function of time. The data used to develop FIG. 41 is provided below in Table 7, below.

TABLE 7

| Time | No structure microneedle | Subcutaneous | DN2 | Subcutaneous | DN3 |
|---|---|---|---|---|---|
| 0 | 0.00 | 0.00 | 0.00 | 0.00 | 0.00 |
| 0.5 | 0.00 | 157.49 | 0.00 | 1611.21 | 0.00 |
| 2 | 0.00 | 3029.07 | 0.00 | 3504.92 | 497.17 |
| 6 | 0.00 | 3545.14 | 338.23 | 3699.24 | 796.64 |
| 12 | 0.00 | 3577.13 | 731.22 | 3571.80 | 1080.60 |
| 24 | 116.78 | 3778.71 | 785.49 | 3464.70 | 1924.24 |
| 48 | 134.23 | 3416.73 | 638.18 | 3885.31 | 1006.95 |
| 72 | 88.68 | 3356.64 | 572.77 | 3803.42 | 1172.67 |

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A drug delivery device comprising:
   a composite microneedle array comprising:
   a microneedle assembly that comprises a plurality of microneedles;
   a film overlaying at least one microneedle of the microneedle assembly, the film having a first surface and a second surface, wherein the first surface of the film is adhered to the microneedle and at least partially conforms thereto, the film comprising a plurality of nanostructures on the second surface of the film arranged to project outward from the second surface of the film, and wherein at least a portion of the nanostructures have a cross-sectional dimension of less than 500 nanometers and greater than 5 nanometers, a height of from 10 nanometers to 1 micrometer, and an aspect ratio of from 0.2 to 5; and a reservoir for holding a drug compound, the reservoir being in fluid connection with the microneedle array.

2. The drug delivery device according to claim 1, wherein at least a portion of the nanostructures of the plurality of nanostructures has a cross-sectional dimension of less than about 400 nanometers and greater than about 10 nanometers.

3. The drug delivery device according to claim 1, wherein the film further comprises a plurality of microstructures on the second surface of the film, each of the nanostructures of the plurality of nanostructures having a cross-sectional dimension smaller than each of the microstructures of the plurality of microstructures.

4. The drug delivery device according to claim 3, wherein the plurality of nanostructures comprise first nanostructures and second nanostructures wherein the second nanostructures have a cross-sectional dimension less than a cross-sectional dimension of the plurality of microstructures and greater than a cross-sectional dimension of the first nanostructures.

5. The drug delivery device according to claim 1, wherein at least a portion of the nanostructures of the plurality of nanostructures has a height of from 100 nanometers to 700 nanometers.

6. The drug delivery device according to claim 1, wherein at least a portion of the nanostructures of the plurality of nanostructures has an aspect ratio of from 0.5 to 3.5.

7. The drug delivery device according to claim 1, further comprising a rate control membrane in fluid communication with the reservoir.

8. The drug delivery device according to claim 7, further comprising a release member that is generally impermeable to the drug compound and positioned adjacent to the rate control membrane.

* * * * *